(12) United States Patent
Edamana et al.

(10) Patent No.: US 8,828,735 B2
(45) Date of Patent: Sep. 9, 2014

(54) VISUAL DETECTION OF FLUORIDE IONS

(75) Inventors: Prasad Edamana, Chennai (IN); Rajamalli Pachaiyappan, Kottappoondi (IN)

(73) Assignee: Indian Institute of Technology Madras, Tamilnadu, Chennai (IN)

( * ) Notice: Subject to any disclaimer, the term of this patent is extended or adjusted under 35 U.S.C. 154(b) by 0 days.

(21) Appl. No.: 13/528,981

(22) Filed: Jun. 21, 2012

(65) Prior Publication Data

US 2013/0344608 A1  Dec. 26, 2013

(51) Int. Cl.
*G01N 21/29* (2006.01)

(52) U.S. Cl.
USPC ............................................... 436/124

(58) Field of Classification Search
CPC ....... G01N 21/29; G01N 21/25; G01N 21/17; G01N 21/00
USPC ........................................................ 436/124
See application file for complete search history.

(56) References Cited

PUBLICATIONS

Rajamilli P. et al, Low Molecular Weight Fluorescent Organogel for Fluoride Ion Detection, Organic Letters, received May 21, 2011, published Jun. 21, 2011, vol. 13, No. 14, p. 3714-3717.*

* cited by examiner

*Primary Examiner* — Christine T Mui
(74) *Attorney, Agent, or Firm* — Pepper Hamilton LLP

(57) ABSTRACT

Dendrimer-hydrazides are coupled to polycyclic aromatic hydrocarbons for use in the visual detection of the presence of low levels of fluoride in a sample The dendrimers can have a phenyl core, a first generation of aralkyl ethers, and an optional second generation of aralkyl ethers. The compounds form gels with solvents. In the presence of fluoride ion, the gels undergo color changes and/or gel to liquid phase change.

8 Claims, 2 Drawing Sheets

VISUAL DETECTION OF FLUORIDE IONS

BACKGROUND

Ground-water is the most dependable and widespread source of drinking water. In many parts of the world it is the only source of water. Despite being a relatively safe source for human consumption, groundwater suffers from various chemical and mineral contaminations including fluoride ions. Long term consumption of such water (fluoride ion concentrations above 1 ppm) can cause damaged and discolored teeth (dental fluorosis) and debilitating bone ailments (skeletal fluorosis) which are irreversible. The only way out is to prevent the intake of fluoride ions. The first and most obvious step towards this is identification of safe sources of groundwater.

Two-thirds of all fluoride salts mined is used in the electrolysis of aluminum and the production of steel. Fluoride salts are also used in the industrial production of ceramics, enamels, glass fibers, cement and agrichemicals. There is a need to monitor levels of fluoride ions for safety not only in drinking water, but in lakes, swimming pools, industrial waste, and agricultural run-off. Thus, there is a growing market for simple and affordable fluoride ion detection systems. Current fluoride detection kits are not well suited for individual/local use, besides being relatively expensive and requiring personnel training in order to be properly used.

SUMMARY

Gelators are of interest as they have a propensity to form a stable three-dimensional (3D) network through weak intermolecular interactions. Gelators described herein selectively react with fluoride ions and provide a change visible to the naked eye. Methods are described for the visual detection of fluoride ions at micromolar concentrations. The easily determined visual changes are a color change, such as yellow to red, and a phase change from a gel to liquid. It is hoped that this inexpensive, effective, and easy to use visual detection will prove advantageous in helping to prevent fluorosis.

A first aspect is a compound that is an alkylene hydrazide of structure (XX) having an acyl dendrimer and an alkylene polycyclic aromatic hydrocarbon. The polycyclic aromatic hydrocarbon is optionally substituted with one or two groups that are independently a trifluoromethyl, trifluoroethyl, nitro, cyano, —OH, or alkyl. The dendrimer can have a phenyl core, a first generation layer of aralkyl ethers bonded to the core and an optional second generation layer of aralkyl ethers bonded to the first generation layer.

A second aspect is a method of using an alkylene hydrazide of structure (XX) for the visual detection of fluoride ions. The method comprises providing a sample suspected of containing fluoride ions, contacting the sample with the alkylene hydrazide, and detecting at least one of a visual color change and a phase change, wherein such change indicates fluoride ions are present in the sample.

A third aspect is a kit for the detection of fluoride ions. The kit comprises a transparent container, an alkylene hydrazide of structure (XX) for the visual detection of fluoride ions, and an acceptable carrier. The acceptable carrier can be at least one solvent.

A fourth aspect is a method of preparing an alkylene hydrazide of structure (XX). The method comprises contacting a polycyclic aromatic hydrocarbon aldehyde with a hydrazide of an acyl dendrimer. The dendrimer can have a phenyl core, a first generation layer of aralkyl ethers bonded to the core and an optional second generation layer of aralkyl ethers bonded to the first generation layer.

DETAILED DESCRIPTION

Figure 1:
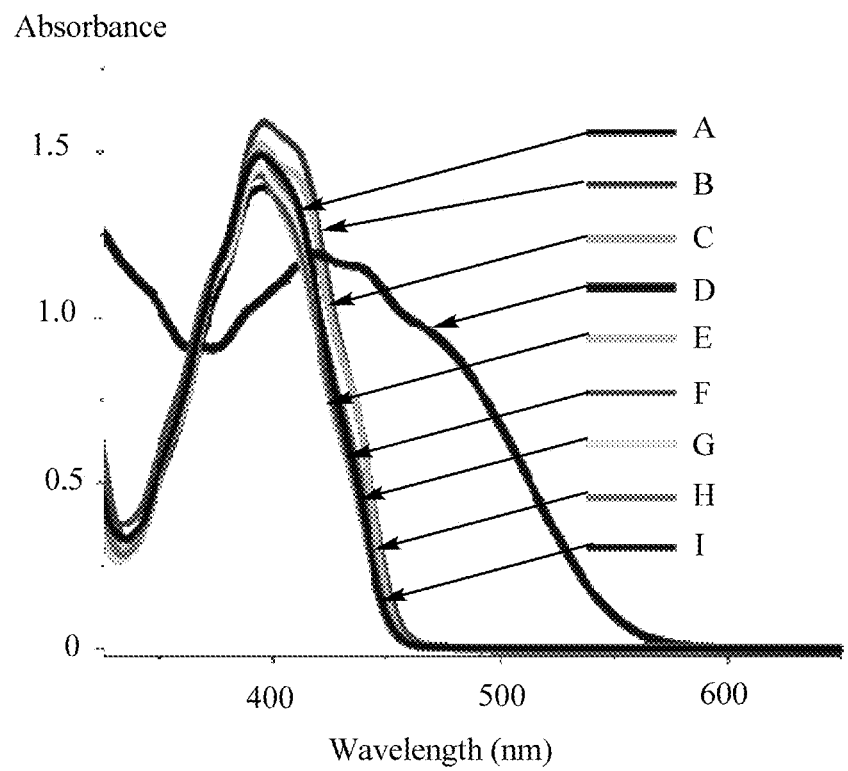
FIG. 1 depicts the UV-Vis Absorption spectra of compound I ($1 \times 10^{-4}$ M) in the presence of 1 equivalent of various anions in tetrahydrofuran at room temperature.

Presently disclosed are compounds and methods for visually detecting fluoride ions in a sample. The disclosed compounds, when bound to fluoride ions, exhibit a color change in the visible spectrum and/or a physical phase change, allowing simple detection of fluoride ions in a sample.

The term "alkyl" or "alkyl group" refers to a branched or unbranched hydrocarbon or group of 1 to 20 carbon atoms, such as but not limited to methyl, ethyl, n-propyl, isopropyl, n-butyl, isobutyl, t-butyl, and the like. "Cycloalkyl" or "cycloalkyl groups" are branched or unbranched hydrocarbons in which all or some of the carbons are arranged in a ring, such as but not limited to cyclopentyl, cyclohexyl, methylcyclohexyl and the like.

The term "aryl" or "aryl group" refers to monovalent aromatic hydrocarbon radicals or groups consisting of one or more fused rings in which at least one ring is aromatic in nature. Aryls may include but are not limited to phenyl, naphthyl, biphenyl ring systems and the like. The aryl group may be unsubstituted or substituted with a variety of substituents including, but not limited to, alkyl, alkenyl, halide, cyano, nitro, hydroxyl, trifluoromethyl, trifluoroethyl, benzylic, alkyl or aromatic ether, nitro, cyano and the like and combinations thereof.

As used herein "aralkyl" or "aralkyl groups" refers to an aryl group as described above attached to an alkyl group as described above. Examples of aralkyl groups include but are not limited to benzyl, 1-phenylethyl, 2-phenylethyl, 3-phenylpropyl, and the like.

The term "aprotic solvent", as used herein, is a solvent that possesses the property of polarity, yet does not have the ability to donate a proton. Suitable aprotic solvents include, N,N-dimethylformamide (DMF), N,N-dimethylacetamide (DMAC), N-methylpyrrolidone (NMP), dimethyl sulfoxide (DMSO), acetonitrile (ACN), tetrahydrofuran, (THF), ethyl acetate (EtOAc), propionitrile, acetone, methyl ethyl ketone, methyl propyl ketone, methyl isobutyl ketone, 2-methoxyethyl acetate, dioxane, pyridine (py), chlorobenzene, anisole, methylene chloride ($CH_2CL_2$), and chloroform ($CHCl_3$), cyclohexane, benzene, toluene, xylene, and carbon tetrachloride.

As used herein, the term "sequestration" is a process of binding of an ion to a compound or compounds, by covalent bond, an ionic bond, a hydrogen bond, and combinations thereof. As used herein, the term "sequester" refers to the formation of the binding interaction between the fluoride and the hydrazide containing compound.

Compounds may also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Examples of prototropic tautomers include, but are not limited to, alkylene hydrazide-acylalkyldiazene pairs,

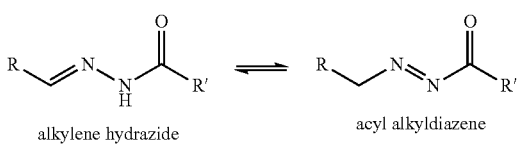

alkylene hydrazide   acyl alkyldiazene ketone-enol pairs, amide-imidic acid pairs, lactam-lactim pairs, amide-imidic acid pairs, enamine-imine pairs, and annular forms where a proton can occupy two or more positions of a heterocyclic system including, but not limited to, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Many geometric isomers of olefins, C=N double bonds, N=N double bonds, amides, and the like can also be present in the compounds described herein, and all such stable isomers are contemplated. Cis and trans geometric isomers of the compounds are also contemplated and can be isolated as a mixture of isomers or as separated isomeric forms. Where a compound capable of stereoisomerism or geometric isomerism is designated in its structure or name without reference to specific R/S or cis/trans configurations, it is intended that all such isomers are contemplated.

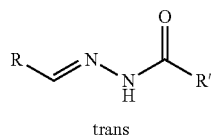

trans

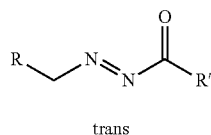

trans

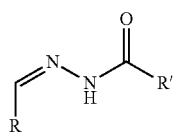

cis

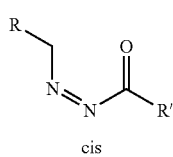

cis

As used herein, "dendrimers" are repetitively branched molecules leading to a monodisperse, tree-like or generational structure. As used herein, dendrimirs are comprised of unit molecules, called "dendrons." A dendrimer is typically symmetric about the core, but asymmetry is acceptable. Dendrimers are also classified by generation, which refers to the number of repeated branching cycles that are performed during its synthesis. For example if a dendrimer is made by convergent synthesis, and the branching reactions are performed onto the core molecule two times, the resulting dendrimer is considered a second generation dendrimer.

Poly(aryl ether) dendrimers with an anthracene moiety attached to the core through a acyl-hydrazone linkage can form an 'instant gel'. The resulting gel undergoes a gel-to-sol transition, accompanied by a color change from deep yellow to bright red, in the presence of fluoride ions. The onset of the color change was noticed at a fluoride ion concentration as low as about 0.1 equivalents with respect to the gelator concentration. This provides an opportunity for the 'naked eye' detection of fluoride ions, which is one of the targeted anions due to its important role in biological systems. The disclosed compounds are the first reported examples of a dendrimer based fluorescent low molecular weight gelator (LMWG) which undergoes a reversible sol-gel transition in the presence of fluoride ions at very low concentrations of the analyte.

First and second generation poly(aryl ether) dendrimers have been prepared, and a polycyclic aromatic hydrocarbon attached to the dendrimer through an acyl-hydrazone spacer unit, according to the chemistry shown in Scheme 1 below.

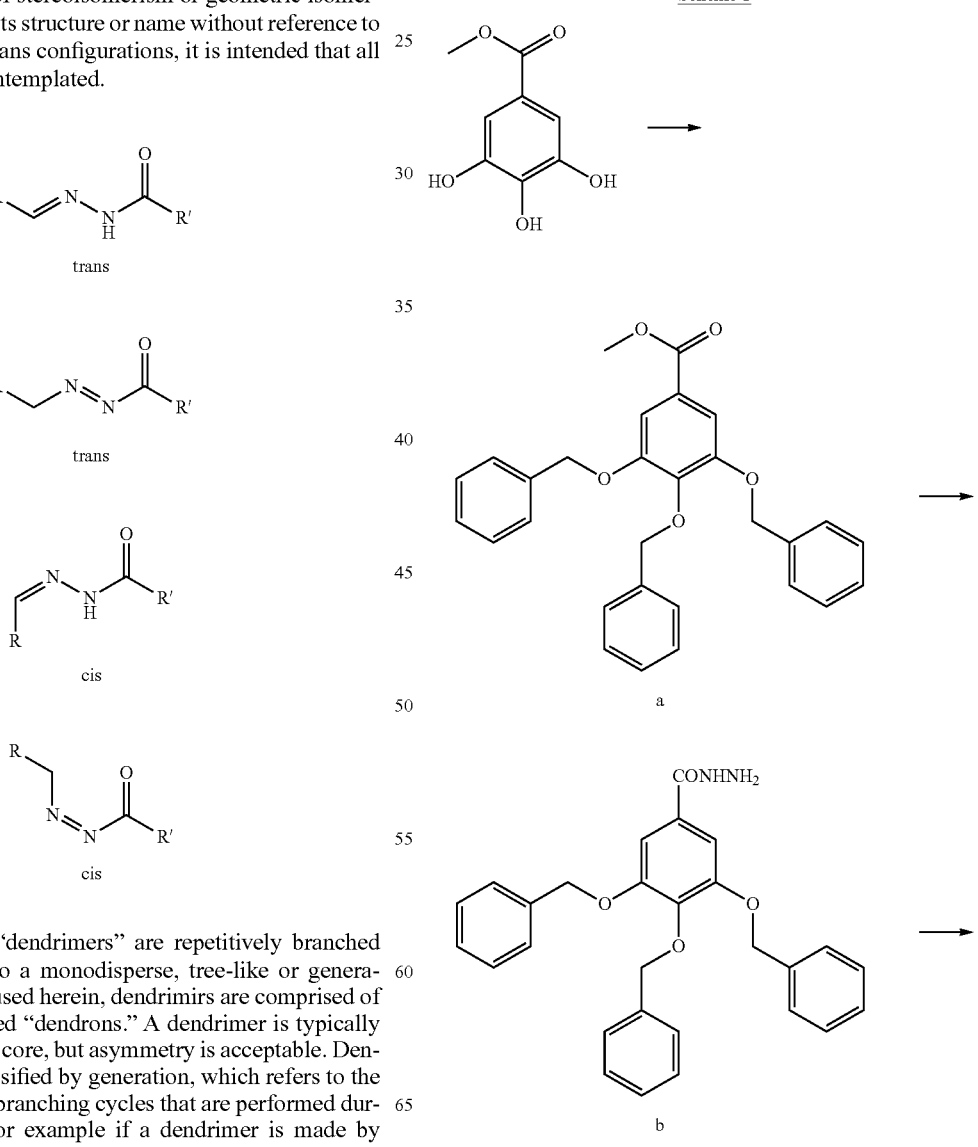

Scheme 1

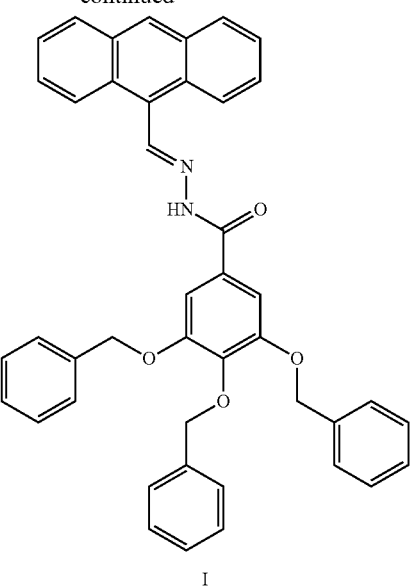

I

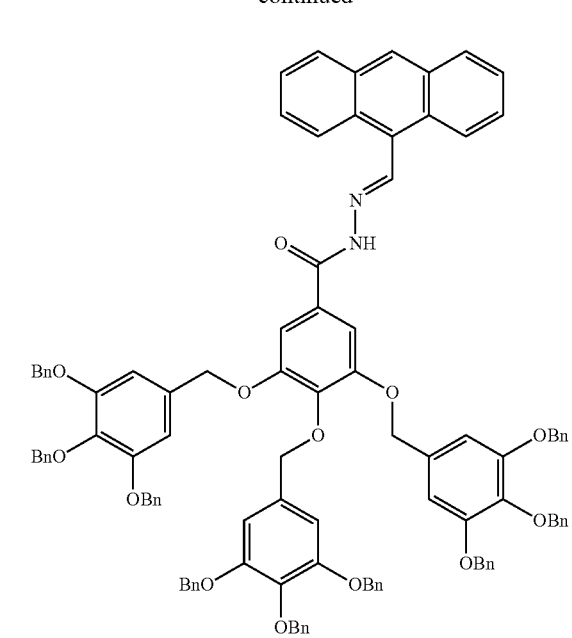

II

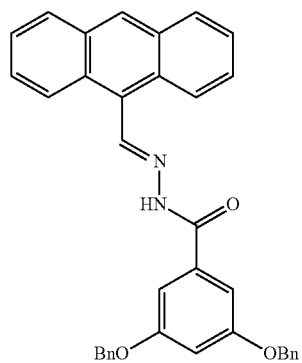

III

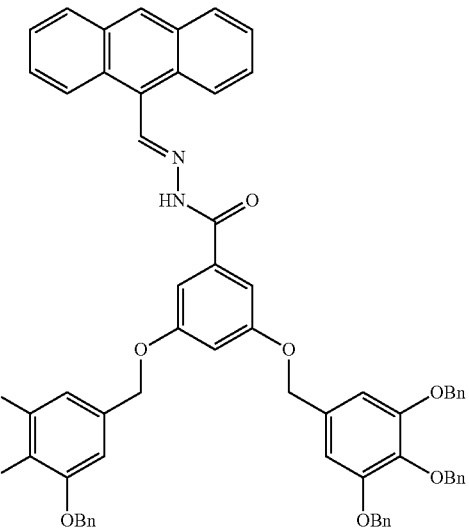

IV

The gelation propensity of the dendrimers in dielectric media was examined in a wide range of solvents and solvent mixtures. The critical gel concentration (CGC) of the compounds was determined in various solvents as well as solvent mixtures, and the values are given in Example 5, Table 1. AB3 type poly(aryl ether) dendrimers form gel in the presence of several organic solvents at a very low CGC (0.4 wt. %). For example, 4 mg of compound I can gel in 1 mL of $CHCl_3$, suggesting that 1895 $CHCl_3$ molecules are immobilized per molecule of compound I. In a similar way, 5005 toluene molecules are immobilized per molecule of compound II, in the gel. Compound II forms a transparent gel in toluene, presumably due to the controlled agglomeration of the sterically encumbered individual dendrimers units. Compound III forms a gel at a relatively higher concentration compared to the other dendrimer derivatives.

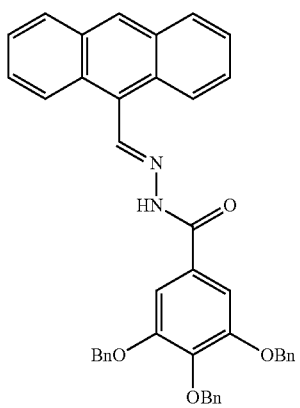

I

Without wishing to be bound to any particular theory, this behavior may be due to the lesser number of aryl groups present in the dendrimers, which play an important role in invoking the gelation through π-π interactions. The role of H-bonding was investigated by infrared spectroscopy. The FT-IR spectrum of compound I shows a single amide band at 1645 cm$^{-1}$ and an intense NH stretching vibration at 3205 cm$^-$. These spectroscopic data are a signature of a network of hydrogen bonded amides. Most likely, gelation occurs through a two-step hierarchical supramolecular mechanism. First, the molecules are assembled through H-bonding and π-π interactions into one-dimensional extended assemblies, followed by the intertwining of the chains together to form a fiber.

The low molecular weight organogels were found to be completely thermo-reversible in organic solvents and solvent mixtures. The gel-sol phase transition temperature (Tgel) was estimated to fall between 60 and 70° C. in a THF/water mixture (0.2-1.2 wt. %). The gel transition temperature typically increases as the concentration of the gel increases.

While the poly(aryl ether) dendrimer derivative shown in FIG. 1 was almost nonfluorescent in solution, a significant enhancement in emission intensity was observed as a result of the gelation. There is essentially no emission from the solution phase under UV and visible light irradiation. Conversely, the gel system emits bright green luminescence under UV irradiation. One explanation for the fluorescence enhancement of the gel systems is gel-induced enhanced emission (GIEE). Molecules of the first aspect exhibited 590-fold enhancement in the emission intensity in the gel compared to that in solution.

The excited state luminescence lifetime of the gels were measured. Fluorescence decays were best fit for a double exponential curve with 7.03 ns (88.77%) and 1.23 ns (11.23%). Structureless luminescence emission from the gel systems (λmax=490 to 505 nm) suggests the formation of a polycyclic aromatic hydrocarbon excimer upon photoexcitation.

The anion binding properties of the gel systems toward a number of selected anions (F$^-$, Cl$^-$, Br$^-$, I$^-$, CH$_3$COO$^-$, H$_2$PO$_4^-$, and HSO$_4^-$) as Bu$_4$N$^+$ salts were examined in THF. The gels show intense variation in their electronic absorption spectra only upon the addition of a fluoride salt, such as tetrabutylammonium fluoride (TBAF) (0.1 equivalent), at room temperature. The presence of F not only changes the color of the system but also disrupts the preformed gel to a solution through slow diffusion of the anion.

Figure 2:
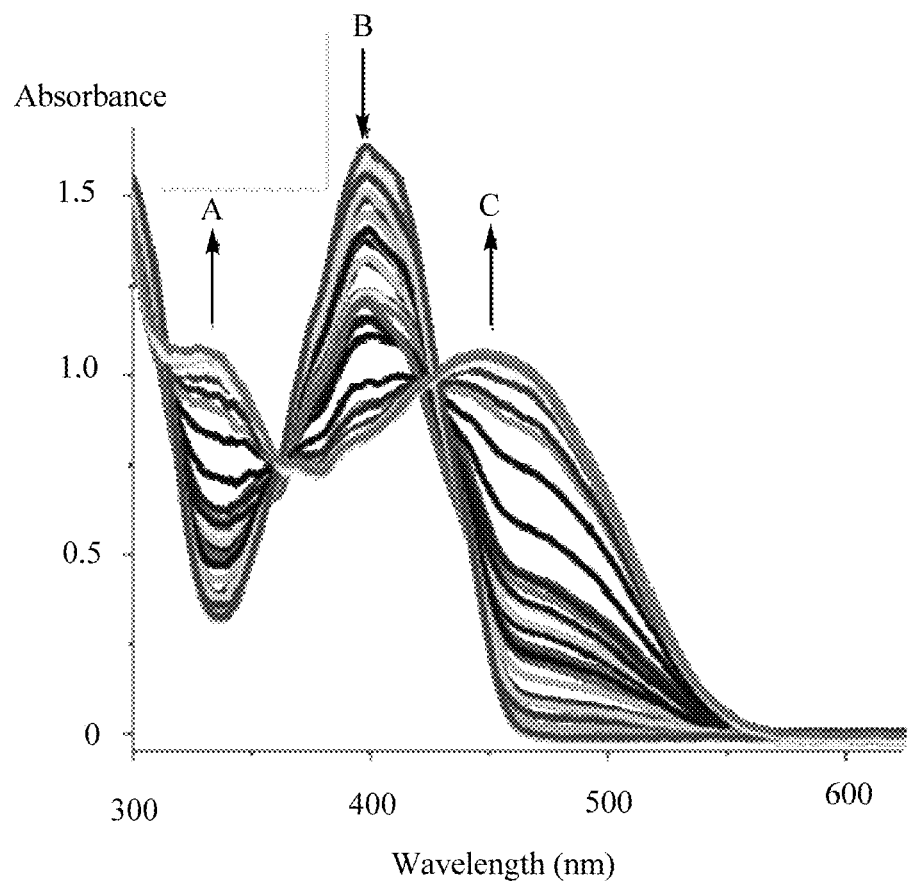
FIG. 2 depicts the UV-Vis spectra changes of compound II ($1 \times 10^{-4}$ M) on addition of aliquot amounts of fluoride ion.
Figure 1:
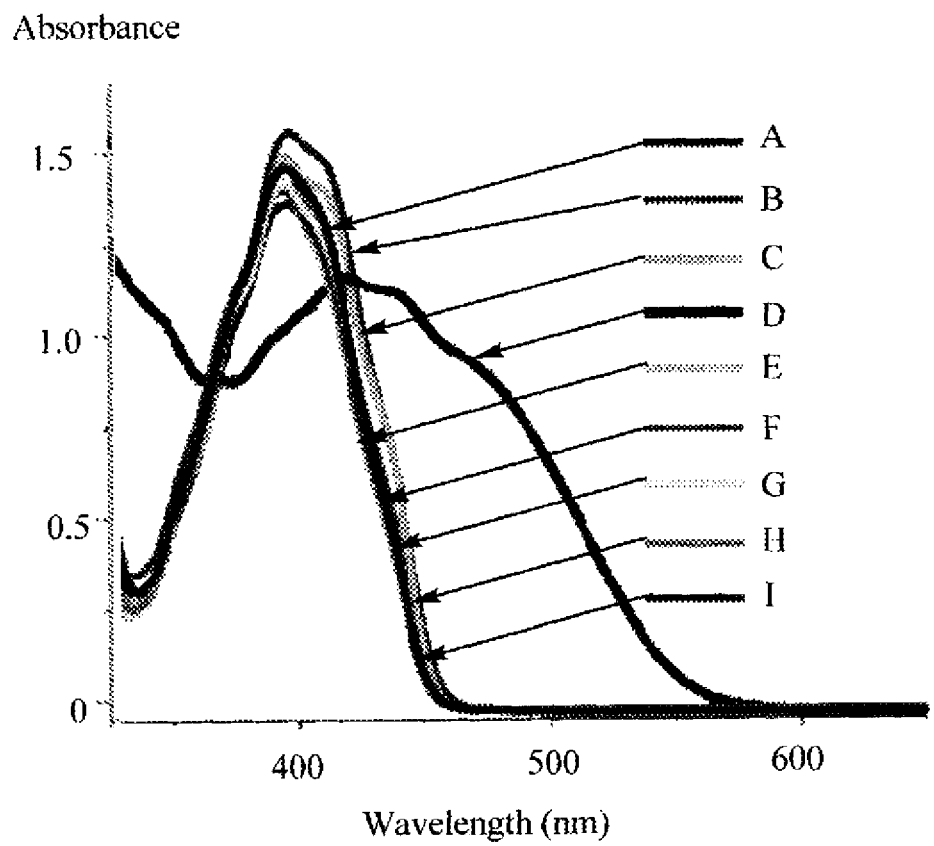

The drastic color change of the gels accompanied by the addition of fluoride ions suggests changes in the electronic structure of the system. The UV-Vis absorption spectra of compound I in THF (1×10$^{-4}$ M) in the presence of one equivalent of various anions were taken at room temperature as shown in FIG. 1. The absorption band of compound I shifted to a longer wavelength only in the presence of fluoride ions. The UV-Vis spectra of compound I in THF (1×10$^{-4}$ M) in the presence of an increasing amount of fluoride ions are shown in FIG. 2. The figure shows a decrease in absorption at wavelength B and growing maxima at A and C. The presence of the isosbestic point between B and C, indicates that the addition of fluoride ions generates a species with increased conjugation. Before the addition of fluoride ions, the $^1$H NMR chemical shift values of —CH=N— and —NH protons in the compounds were at 9.65 and 12.05 ppm, respectively. After addition of one equivalent of fluoride ions, the NH signal disappeared that may indicate deprotonation of the NH group.

This could be, without being bound to any particular theory, through proton abstraction from the gel by the fluoride ion. Subsequently, the H-bonding in the gel is weakened, leading to the gel-sol conversion. The Job plot analysis suggested the formation of a complex with a 1:1 stoichiometric ratio between the gelator and anion with an association constant value of 2.9×10$^{-4}$ M$^{-1}$. The increased conjugation was further corroborated by the observation of the structured vibronic emission from the anthracene unit of compound I, which appeared at a red-shifted wavelength in the presence of fluoride ions. Compound I gel (yellow) in THF was a red-colored liquid upon addition of fluoride ion. The low molecular weight fluorescent organogel system can act as an efficient 'naked eye' detecting system for fluoride ions at very low concentrations of the analyte (see Scheme 2).

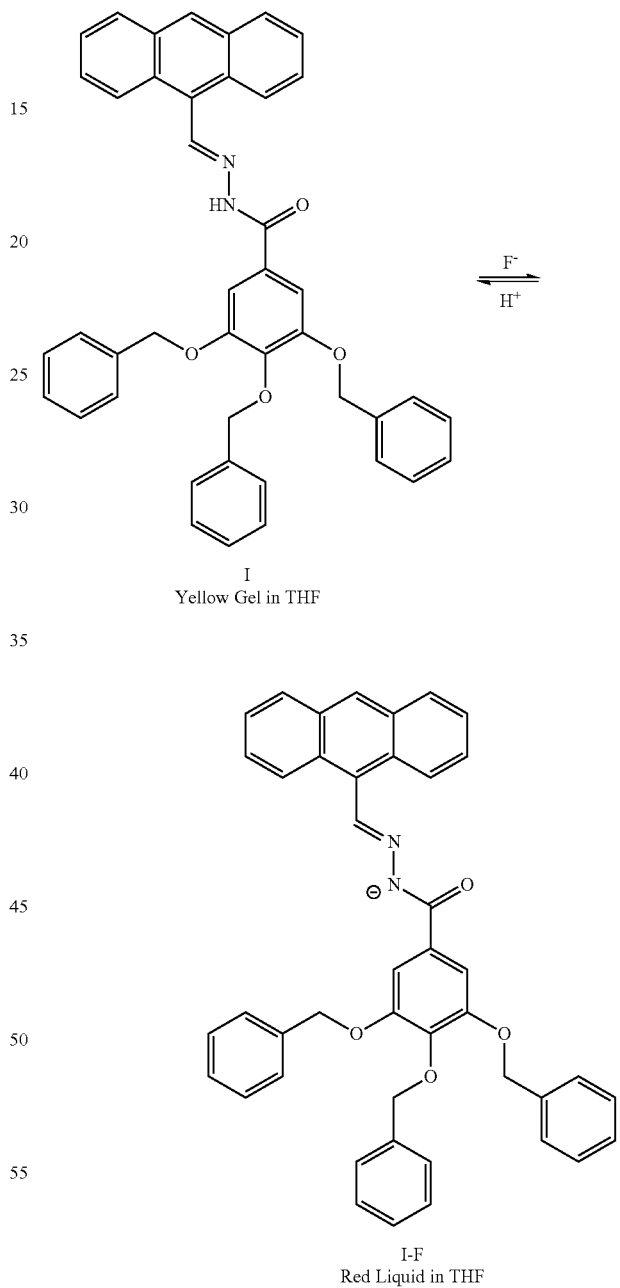

Scheme 2

I
Yellow Gel in THF

I-F
Red Liquid in THF

In a first aspect, embodiments of various compounds, tautomers, and salts thereof are provided. Where a variable is not specifically recited, the variable can be any option described herein, except as otherwise noted or dictated by context.

In some embodiments, a compound is provided having the formula (XX):

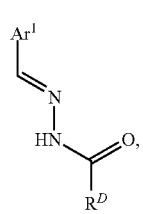

(XX)

a tautomer thereof, or a salt thereof, wherein $Ar^1$ is a —$C_{10}$-$C_{36}$ polycyclic aromatic hydrocarbon, optionally substituted with one or two $R^o$ groups; each $R^o$ is independently trifluoromethyl, trifluoroethyl, nitro, cyano, —OH, or —$C_1$-$C_{20}$alkyl; and $R^D$ is a dendrimer comprising a phenyl core, a first generation layer of —O—($C_1$-$C_{12}$)alkyl-aryl bonded to the core, and an optional second generation layer of —O—($C_1$-$C_{12}$)alkyl-aryl bonded to the first generation layer aryl. In other embodiments, $R^D$ is a dendrimer comprising a phenyl core, a first generation layer of —O—($C_1$-$C_6$)alkyl-aryl bonded to the core, and an optional second generation layer of —O—($C_1$-$C_6$)alkyl-aryl bonded to the first generation layer aryl. Some other embodiment provide a compound having the formula (XX), a tautomer thereof, or a salt thereof, wherein $Ar^1$ is a —$C_{10}$-$C_{36}$ polycyclic aromatic hydrocarbon.

Some embodiments include the compound of formula (XX) having is according to formula (XXI):

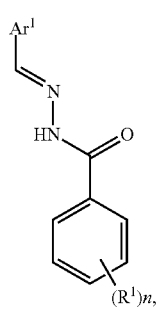

(XXI)

a tautomer thereof, or an acceptable salt thereof, wherein n is 2 or 3; $Ar^1$ is naphthalene, anthracene, phenanthrene, chrysene, pyrene, tetracene, perylene, decacyclene or triphelene, each optionally substituted with one or two $R^o$ groups; each $R^o$ is independently trifluoromethyl, trifluoroethyl, nitro, cyano, —OH, or —$C_1$-$C_{20}$alkyl; $R^1$ is —O—($C_1$-$C_{12}$)alkyl-aryl, each aryl optionally substituted with up to three $R^2$ groups, wherein each $R^2$ is independently —O—($C_1$-$C_{12}$) alkyl-aryl. In other embodiments, $R^1$ is —O—($C_1$-$C_6$)alkyl-aryl, each aryl optionally substituted with up to three $R^2$ groups, wherein each $R^2$ is independently —O—($C_1$-$C_6$) alkyl-aryl. In two embodiments, a compound of formula (XX) or (XXI) wherein $Ar^1$ is anthracene, optionally substituted with one or two $R^o$ groups. In another embodiment, compounds of the formula (XXI), or a tautomer thereof, or a salt thereof, wherein n is 2 or 3; $Ar^1$ is naphthalene, anthracene, phenanthrene, chrysene, pyrene, tetracene, perylene, decacyclene or triphelene; $R^1$ is —O—($C_1$-$C_{12}$) alkyl-aryl, each aryl optionally substituted with up to three —O—($C_1$-$C_{12}$)alkyl-aryl.

In another embodiment, the compound of formula (XX) is according to formula (XXII),

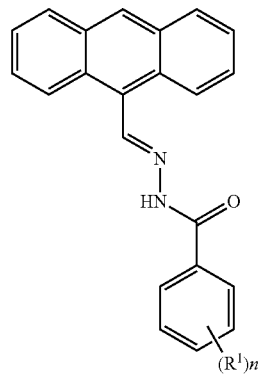

(XXII)

or a tautomer thereof, or an acceptable salt thereof, wherein n is 2 or 3;

$Ar^1$ is naphthalene, anthracene, phenanthrene, chrysene, pyrene, tetracene, perylene, decacyclene or triphelene; $R^1$ is —O—($C_1$-$C_{12}$)alkyl-aryl, each aryl optionally substituted with up to three —O—($C_1$-$C_{12}$)alkyl-aryl. In other embodiments, $R^1$ is —O—($C_1$-$C_6$)alkyl-aryl, each aryl optionally substituted with up to three —O—($C_1$-$C_6$)alkyl-aryl. In another embodiment, the compound of formula (XXII), wherein $R^2$ is —O—$CH_2$-phenyl.

In another embodiment, the compound of formula (XX) is according to formula (XXIII), or a tautomer thereof, or a salt thereof, wherein

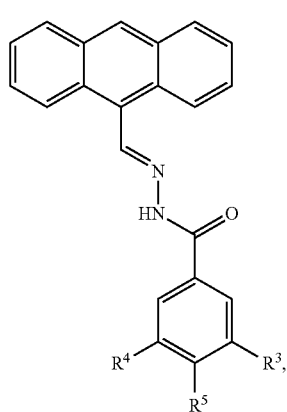

(XXIII)

$R^3$, $R^4$, and $R^5$ are independently hydrogen, or —O—($C_1$-$C_2$) alkyl-aryl, each aryl optionally substituted with 0, 1, 2, or 3 $R^2$ group; and provided that no more than one of $R^3$, $R^4$, $R^5$ is hydrogen. In another embodiment, the compound of formula (XXIII), or a tautomer thereof, or a salt thereof, wherein $R^3$, $R^4$, and $R^5$ are independently hydrogen, or —O—$CH_2$-aryl; and provided that no more than one of $R^3$, $R^4$, $R^5$ is hydrogen. In another embodiment, the compound of formula (XXIII), or a tautomer thereof, or a salt thereof, wherein $R^3$, $R^4$, and $R^5$ are independently hydrogen, or —O—$CH_2$-phenyl; and provided that no more than one of $R^3$, $R^4$, $R^5$ is hydrogen.

In another embodiment, the compound of formula (XX), is according to the formula (XXIV),

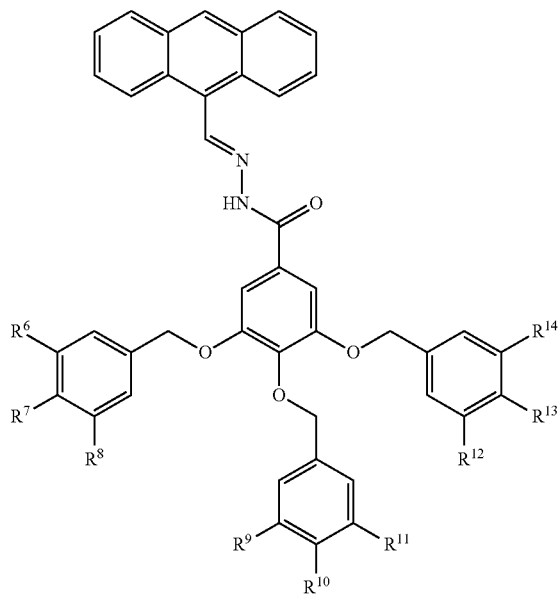

(XXIV)

or a tautomer thereof, or an acceptable salt thereof, wherein $R^6, R^7, R^8, R^9, R^{10}, R^{11}, R^{12}, R^{13}$, and $R^{14}$ are independently hydrogen or —O—$(C_1$-$C_2)$alkyl-aryl. In another embodiment, the compound of formula (XXIV), or a tautomer thereof, or an acceptable salt thereof, wherein $R^6, R^7, R^8, R^9, R^{10}, R^{11}, R^{12}, R^{13}$, and $R^{14}$ independently hydrogen or —O—$CH_2$-aryl. In another embodiment, the compound of formula (XXIV), or a tautomer thereof, or an acceptable salt thereof, wherein $R^6, R^7, R^8, R^9, R^{10}, R^{11}, R^{12}, R^{13}$, and $R^{14}$ are independently hydrogen or —O—$CH_2$-phenyl. In another embodiment, the compound of formula (XXIV), or a tautomer thereof, or an acceptable salt thereof, wherein $R^6, R^7, R^8, R^9, R^{10}, R^{11}, R^{12}, R^{13}$, and $R^{14}$ are independently hydrogen or —O—$CH_2$-aryl; no more than one of $R^6, R^7$, or $R^8$ is hydrogen; no more than one of $R^9, R^{10}$, and $R^{11}$ is hydrogen; and no more than one of $R^{12}, R^{13}$, and $R^{14}$ is hydrogen. In another embodiment, the compound of formula (XXIV), or a tautomer thereof, or an acceptable salt thereof, wherein $R^6, R^7, R^8, R^9, R^{10}, R^{11}, R^{12}, R^{13}$, and $R^{14}$ are independently hydrogen or —O—$CH_2$-phenyl; no more than one of $R^6, R^7$, or $R^8$ is hydrogen; no more than one of $R^9, R^{10}$, and $R^{11}$ is hydrogen; and no more than one of $R^{12}, R^{13}$, and $R^{14}$ is hydrogen. In another embodiment, the compound of formula (XXIV), wherein $R^6, R^8, R^9, R^{11}, R^{12}$, and $R^{14}$ are independently hydrogen or —O—$CH_2$—phenyl; and $R^7, R^{10}$, and $R^{13}$ are hydrogen.

In another embodiment, the compound of formula (XX) is according to formula (XXV),

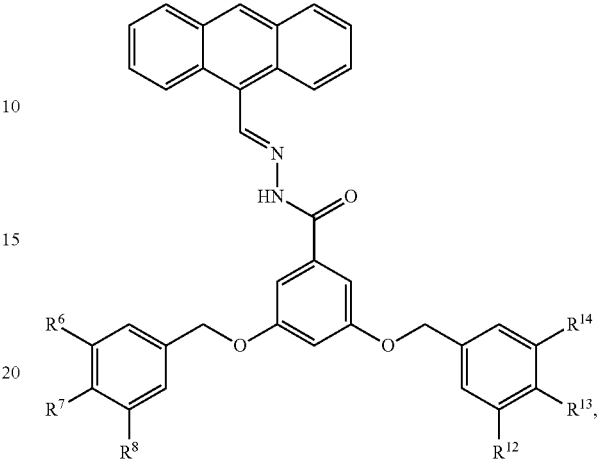

(XXV)

or a tautomer thereof, or an acceptable salt thereof, wherein $R^6, R^7, R^8, R^{12}, R^{13}$, and $R^{14}$ are independently hydrogen or —O—$(C_1$-$C_2)$alkyl-aryl. In another embodiment, the compound of (XXV), or a tautomer thereof, or an acceptable salt thereof, wherein $R^6, R^7, R^8, R^{12}, R^{13}$, and $R^{14}$ are independently hydrogen or —O—$CH_2$-aryl. In another embodiment, the compound of (XXV), or a tautomer thereof, or an acceptable salt thereof, wherein $R^6, R^7, R^8, R^{12}, R^{13}$, and $R^{14}$ are independently hydrogen or —O—$CH_2$-phenyl. In another embodiment, the compound of (XXV), or a tautomer thereof, or an acceptable salt thereof, wherein $R^6, R^8, R^{12}$, and $R^{14}$ are —O—$CH_2$-aryl; and $R^7$=$R^{13}$ is hydrogen. In another embodiment, the compound of (XXV), or a tautomer thereof, or an acceptable salt thereof, wherein $R^6, R^8, R^{12}$, and $R^{14}$ are —O—$CH_2$-phenyl; and $R^7$=$R^{13}$ is hydrogen. In another embodiment, the compound of formula (XX), defined as N-(anthracen-9-ylmethylene)-3,4,5-tris(benzyloxy)benzohydrazide; N-(anthracen-9-ylmethylene)-3,5-bis(benzyloxy)benzohydrazide; N-(anthracen-9-ylmethylene)-3,4,5-tris(3,4,5-tris(benzyloxy)benzyloxy)benzohydrazide; N-(anthracen-9-ylmethylene)-3,5-bis(3,5-bis(benzyloxy)benzyloxy)benzohydrazide; or a tautomer thereof, or an acceptable salt thereof.

In one embodiment, the compound of formula (XX) can, or is characterized by its ability to, selectively sequester fluoride ions. In another embodiment of, the compound of formula (XX) can, or is characterized by its ability to, undergo a gel to liquid phase change upon fluoride ion sequestration. In another embodiment, the compound of formula (XX) can, or is characterized by its ability to, undergo a color change upon fluoride ion sequestration. In any of the above embodiments, the sequestering or sequestration of fluoride ion is between about 0.1 and 1 equivalents fluoride ion per equivalent of compound. In one embodiment, the sequestering or sequestration is between about 0.1 and 10 equivalents fluoride ion per equivalent of compound. In one embodiment the sequestering or sequestration of fluoride ions is between about 0.1 and 20 equivalents fluoride ion per equivalent of compound. Specific examples of the sequestering/sequestration ranges include about 0.01 equivalents fluoride ion, about 0.05 equivalents fluoride ion, 0.1 equivalents fluoride ion, about 1 equivalent fluoride ion, about 10 equivalents fluoride ion, about 1000 equivalents fluoride ion per equivalent of compound or compounds and ranges between any two of these values.

In a second aspect, embodiments of various methods for detecting fluoride ions using various compounds, tautomers, and salts thereof are provided. Where a variable is not specifically recited, the variable can be any option described herein, except as otherwise noted or dictated by context. The method comprises providing a sample suspected of containing fluoride ions; contacting the sample with a compound according to the formula (XX)

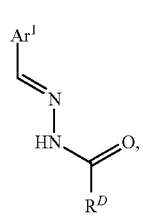
(XX)

a tautomer thereof, or a salt thereof, wherein $Ar^1$ is a $—C_{10}$-$C_{36}$ polycyclic aromatic hydrocarbon, optionally substituted with one or two $R^0$ groups; each $R^0$ is independently trifluoromethyl, trifluoroethyl, nitro, cyano, —OH, or —$C_1$-$C_{20}$alkyl; $R^D$ is a dendrimer comprising a phenyl core, a first generation layer of —O—($C_1$-$C_{12}$)alkyl-aryl bonded to the core, and an optional second generation layer of —O—($C_1$-$C_{12}$)alkyl-aryl bonded to the first generation layer aryl; and detecting at least one of a visual color change and a phase change, wherein such change indicates fluoride ions are present in the sample.

In other embodiments, $R^D$ is a dendrimer comprising a phenyl core, a first generation layer of —O—($C_1$-$C_6$)alkyl-aryl bonded to the core, and an optional second generation layer of —O—($C_1$-$C_6$)alkyl-aryl bonded to the first generation layer aryl. In one embodiment, sample is aqueous. In one embodiment, the contacting further comprises the presence of water. In another embodiment, the phase change is from a gel to a liquid. In one embodiment, the visual color change is a red-shift.

In one embodiment, the fluoride ions are present in the sample at about 1 micromolar concentration range to 1 molar, or about 1 micromolar to 1 millimolar. Specific examples of the concentration include about 1 micromolar, about 10 micromolar, about 100 micromolar, about 1 millimolar, about 1 molar, and ranges between any two of these values. In one embodiment, the fluoride ions are present in the sample at a concentration of at least about 1 micromolar.

In one embodiment, the fluoride ions are present in the sample at about 0.01 equivalents per equivalent of compound, about 0.05 equivalents per equivalent of compound, about 0.1 equivalents per equivalent of compound, about 1 equivalent per equivalent of compound, about 10 equivalents per equivalent of compound, or about 1000 equivalents per equivalent of compound. Specific examples of the concentration include about 0.01 equivalents, 0.05 equivalents, 0.1 equivalent, 1 equivalent, about 10 equivalents, about 1000 equivalents per equivalent of compound, and ranges between any two of these values. In one embodiment, the fluoride ions are present at a concentration of at least 0.1 equivalents per equivalent of compound.

In one embodiment, the fluoride ions are between about 0.1 and 1 equivalents per equivalent of compound. In one embodiment, the fluoride ions are between about 0.1 and 10 equivalents per equivalent of compound. In one embodiment, the fluoride ions are between about 0.1 and 20 equivalents per equivalent of compound.

In one embodiment, the detecting is equal to or at least 1,000 fold more selective for the fluoride ions than to anions selected from the group consisting of chloride, bromide, iodide, perchlorate, acetate, dihydrogen phosphate, hydrogen phosphate, phosphate, bisulfate, sulfate, and combinations thereof. In one embodiment, the detecting is equal to or at least 100 fold more selective for the fluoride ions than to anions selected from the group consisting of chloride, bromide, iodide, perchlorate, acetate, dihydrogen phosphate, hydrogen phosphate, phosphate, bisulfate, sulfate, and combinations thereof. In one embodiment, the detecting is equal to or at least 10 fold more selective for the fluoride ions than to anions selected from the group consisting of chloride, bromide, iodide, perchlorate, acetate, dihydrogen phosphate, hydrogen phosphate, phosphate, bisulfate, sulfate, and combinations thereof.

In another embodiment, the compound is solvated. In another embodiment, the compound is solvated with at least one aprotic solvent. In another embodiment, the compound is solvated with at least one solvent selected from the group consisting of water, methanol, ethanol, acetone, dimethylformamide, dimethyl sulfoxide, acetonitrile, ethyl acetate, cyclohexane, benzene, toluene, chlorobenzene, benzyl alcohol, xylene, anisole, pyridine, tetrahydrofuran, dioxane, methylene chloride, chloroform, and carbon tetrachloride. In another embodiment, the compound is solvated with at least one solvent selected from the group consisting of acetone, dimethylformamide, dimethyl sulfoxide, acetonitrile, ethyl acetate, benzene, toluene, chlorobenzene, xylene, anisole, pyridine, tetrahydrofuran, dioxane, methylene chloride, and chloroform. In another embodiment, the compound is solvated with at least one solvent selected from the group consisting of dimethyl sulfoxide, N,N-dimethylformamide, tetrahydrofuran, and acetonitrile.

In another embodiment, the compound is solvated with tetrahydrofuran. In another embodiment, the compound is solvated in a methanol and chloroform at about a 1:1 v/v ratio. In another embodiment, the compound is solvated in water and a solvent at about a 1:1 v/v ratio, wherein the solvent is at least one solvent selected from the group consisting of methanol, tetrahydrofuran, dioxane, dimethyl sulfoxide, acetonitrile, or dimethylformamide.

In a third aspect, various kits assembled for detecting fluoride ions using various compounds, tautomers, and salts thereof are provided. Where a variable is not specifically recited, the variable can be any option described herein, except as otherwise noted or dictated by context. The kit comprises the components of a container; a compound according to formula (XX),

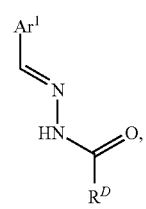
(XX)

a tautomer thereof, or a salt thereof, wherein $Ar^1$ is a $—C_{10}$-$C_{36}$ polycyclic aromatic hydrocarbon, optionally substituted with one or two $R^0$ groups; each $R^0$ is independently trifluoromethyl, trifluoroethyl, nitro, cyano, —OH, or —C$_1$-C$_{20}$alkyl; R$^D$ is a dendrimer comprising a phenyl core, a first generation layer of —O—(C$_1$-C$_{12}$)alkyl-aryl bonded to the core, and an optional second generation layer of —O—(C$_1$-C$_{12}$)alkyl-aryl bonded to the first generation layer aryl; and an acceptable carrier comprising at least one solvent. In some embodiments, the container is transparent.

In another embodiment, the kit comprises the components of a container; a compound according to formula (XXI), a tautomer thereof, or a salt thereof, wherein Ar$^1$ is an anthracene; R$^D$ is a dendrimer comprising a phenyl core, a first generation layer of —O—(C$_1$-C$_{12}$)alkyl-aryl bonded to the core, and an optional second generation layer of —O—(C$_1$-C$_{12}$)alkyl-aryl bonded to the first generation layer aryl; and an acceptable carrier comprising at least one solvent. In some embodiments, the container is transparent.

In other embodiments, R$^D$ is a dendrimer comprising a phenyl core, a first generation layer of —O—(C$_1$-C$_6$)alkyl-aryl bonded to the core, and an optional second generation layer of —O—(C$_1$-C$_6$)alkyl-aryl bonded to the first generation layer aryl. In one embodiment, the acceptable carrier is at least one solvent selected from the group consisting of water, methanol, ethanol, acetone, ethyl acetate, cyclohexane, benzene, toluene, chlorobenzene, benzyl alcohol, xylene, anisole, pyridine, dimethyl sulfoxide, N,N-dimethylformamide, acetonitrile, tetrahydrofuran, dioxane, methylene chloride, chloroform, and carbon tetrachloride and combinations thereof. In one embodiment, the acceptable carrier is at least one solvent selected from the group consisting of acetone, ethyl acetate, benzene, toluene, chlorobenzene, xylene, anisole, pyridine, dioxane, dimethyl sulfoxide, N,N-dimethylformamide, tetrahydrofuran, and acetonitrile, methylene chloride, chloroform, and combinations thereof. In another embodiment, the acceptable carrier is at least one solvent selected from the group consisting of dimethyl sulfoxide, N,N-dimethylformamide, tetrahydrofuran, and acetonitrile.

In a fourth aspect, various methods of preparing various compounds, tautomers, and salts thereof are provided. Where a variable is not specifically recited, the variable can be any option described herein, except as otherwise noted or dictated by context. In one embodiment, the method comprises contacting a C$_{10}$-C$_{36}$ polycyclic aromatic hydrocarbon aldehyde with a hydrazide of the following structure

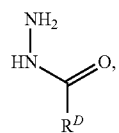

(XXVI)

a tautomer thereof, or a salt thereof, wherein R$^D$ is a dendrimer comprising a phenyl core, a first generation layer of —O—(C$_1$-C$_{12}$)alkyl-aryl bonded to the core, and an optional second generation layer of —O—(C$_1$-C$_{12}$)alkyl-aryl bonded to the first generation layer aryl.

In other embodiments, R$^D$ is a dendrimer comprising a phenyl core, a first generation layer of —O—(C$_1$-C$_6$)alkyl-aryl bonded to the core, and an optional second generation layer of —O—(C$_1$-C$_6$)alkyl-aryl bonded to the first generation layer aryl. In one embodiment, the C$_{10}$-C$_{36}$ polycyclic aromatic hydrocarbon aldehyde is anthracene-9-carbaldehyde. In other embodiments, the C$_{10}$-C$_{36}$ polycyclic aromatic hydrocarbon aldehyde is anthracene-1-carbaldehyde or anthracene-2-carbaldehyde.

One embodiment comprises contacting anthraldehyde and a hydrazide of the following structure (XXVII),

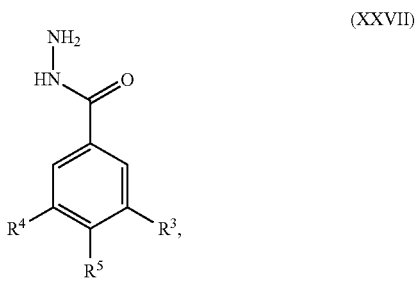

wherein R$^3$, R$^4$, and R$^5$ are independently hydrogen, or —O—(C$_1$-C$_2$)alkyl-aryl, each aryl optionally substituted with 0, 1, 2, or 3 R$^2$ group; and provided that no more than one of R$^3$, R$^4$, R$^5$ is hydrogen.

One embodiment comprises contacting the anthraldehyde and the hydrazide and a carrier, wherein the carrier comprises at least one solvent selected from the group consisting of methanol, ethanol, cyclohexane, benzene, toluene, xylene, methylene chloride, chloroform, carbon tetrachloride, dimethyl sulfoxide, N,N-dimethylformamide, tetrahydrofuran, and acetonitrile. In another embodiment, the carrier comprises at least one solvent selected from the group consisting of dimethyl sulfoxide, N,N-dimethylformamide, tetrahydrofuran, and acetonitrile.

In one embodiment, the anthraldehyde is 9-anthraldehyde. In other embodiments, the anthraldehyde is 1-anthraldehyde or 2-anthraldehyde. In one embodiment, the method further comprises reacting hydrazine hydrate with a first generation layer dendrimer ester (represented by a in Scheme 3) to produce an acyl hydrazide (represented by b). In another embodiment, the method further comprises the alkylation of an alkyl hydroxybenzoate with an aralkyl halide to form a first generation dendrimer.

Scheme 3

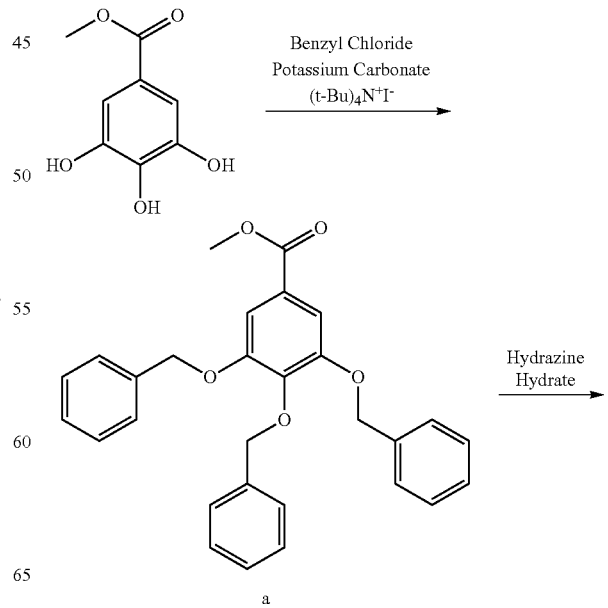

-continued

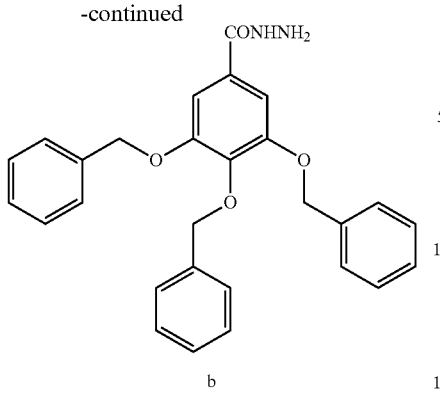

b

In one embodiment, the method further comprises reacting hydrazine hydrate with a second generation layer dendrimer ester (represented by e) to produce an acyl hydrazide (represented by f) (as shown in Scheme 4). In another embodiment, the method further comprises alkylating an alkyl hydroxybenzoate with a dendron aralkyl halide (represented by d) to form a second generation dendrimer, wherein the dendron aralkyl halide has aralkyl ether substituents (as shown in Scheme 5). In another embodiment, the method further comprises preparing the dendron aralkyl halide from an alkyl (aralkylether)benzoate (represented by a) followed by reduction to the benzyl alcohol (represented by c) and subsequent formation of the benzyl halide (represented by d).

Scheme 4

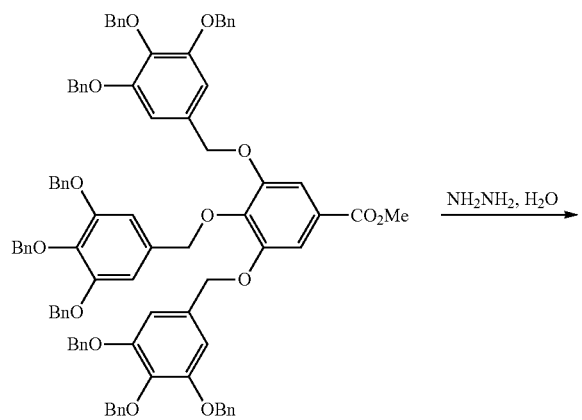

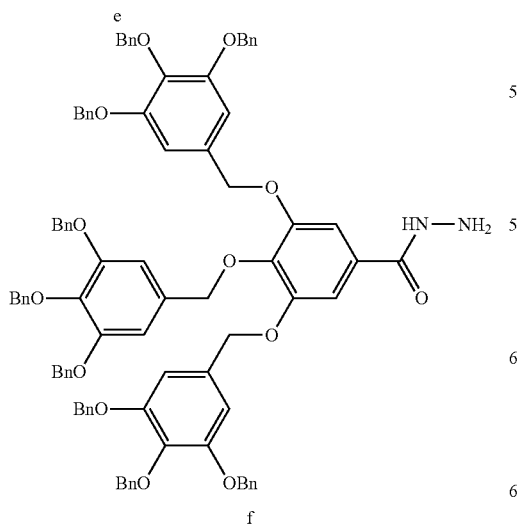

Scheme 5

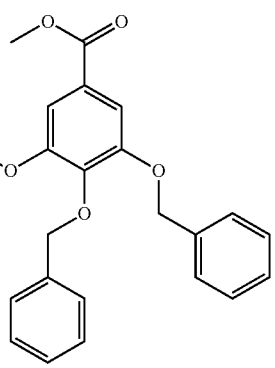

a

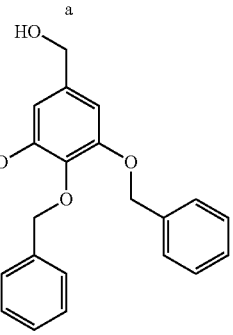

c

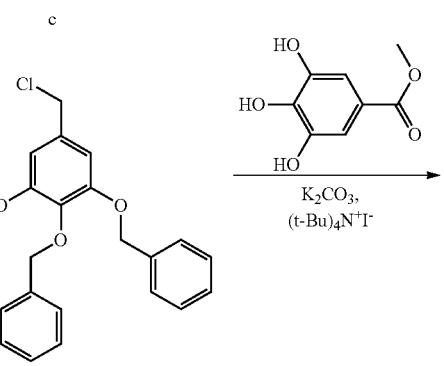

d

EXAMPLES $^1$H and $^{13}$C NMR data were collected on a Bruker 400 MHz spectrometer ($^1$H: 400 MHz; $^{13}$C: 100 MHz). Mass spectra were recorded using Micromass Q-TOF mass spectrometer and Voyager-DE PRO MALDI/TOF mass spectrometer with α-cyano-4-hydroxylcinnamic acid (CCA) as the matrix. IR spectrum was recorded using Jasco FT/IR-4100 spectrometer. Luminescence experiments were carried out on a Horiba Jobin Yvon Fluoromax-4 fluorescence spectrophotometer. The fluorescence decay measurements were carried out by the time correlated single-photon counting technique (TC-SPC) with a micro channel plate photomultiplier tube (MCP-PMT) as detector and pico second laser as excitation source (model 5000 U, IBH, UK). The scanning electron microscopic studies were carried out using a FEI-Quanta Microscope. AFM samples were prepared by spin-coating method on silicon wafer and images were recorded using Park-system XE-100 in the non-contact mode regime. Powder-XRD patterns were recorded on a Bruker D8 Advance X-ray diffractometer using Cu—Kα radiation (λ=1.54178 Å).

General Synthesis:

A mixture of the poly(aryl ether) dendron derivative and polycyclic aromatic hydrocarbon carboxaldehyde (1:1 equivalents) was stirred in a chloroform-methanol mixture (1:1% v/v) for 1 hour at room temperature to yield a robust gel in the reaction flask. The product was then characterized, for example by NMR, mass, and FT-IR spectroscopic techniques. Reaction typically suggests relatively high transformation to the acylhydrazone derivative.

The 'instant gel' from the chloroform-methanol mixture may be dried under vacuum and then dissolved in a selected solvent or solvent mixture by heating. The homogeneous solution may be sonicated and cooled to room temperature to obtain a gel.

Example 1

Synthetic Procedure for Compound I (Scheme 6)

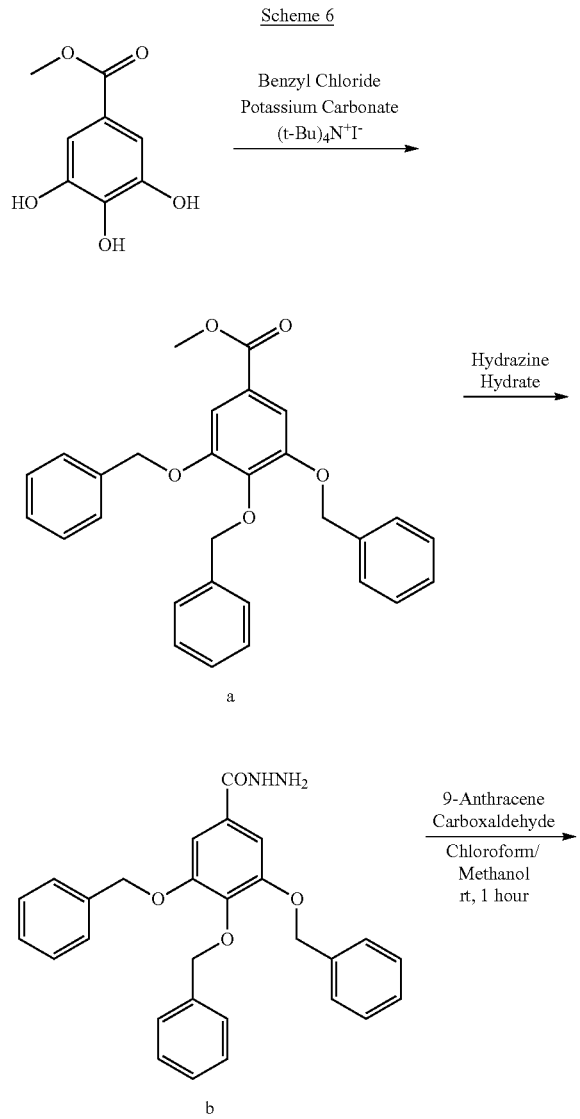

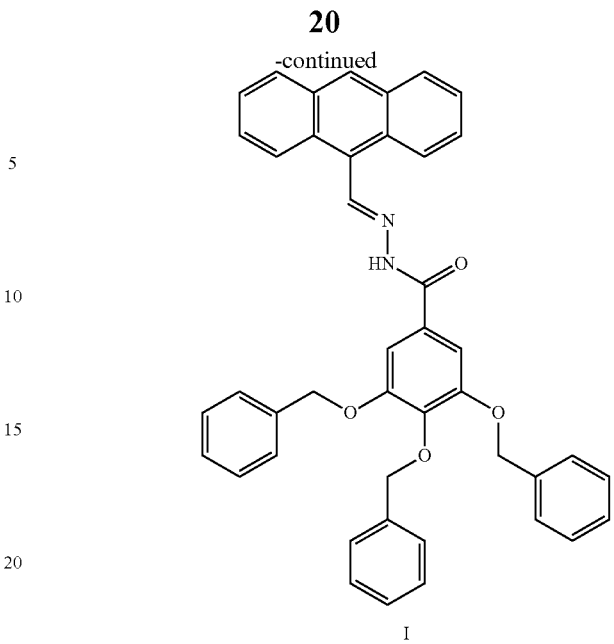

Preparation of (AB)$_3$ G$_1$-COOCH$_3$ (a)

Methyl-3,4,5-trihydroxybenzoate (9 g, 0.045 mole) and potassium carbonate (24.84 g, 0.18 mole) were taken in 130 mL of 1,4-dioxane in a 250 mL round bottom flask. Benzyl chloride (33 mL, 0.135 mole) was added to the above reaction mixture, followed by the addition of a catalytic amount of tertiary butyl ammonium iodide (1.4 g, 0.0045 mole). The solution was heated to refluxing condition along with stiffing for 24 hours. The solvent was then removed under reduced pressure using a rotary evaporator, affording an oily substance, which turned into a solid upon standing. The solid was recrystallized from methanol to yield the product {(AB)$_3$ G$_1$-COOCH$_3$} (18.5 g, 90.5%); $^1$H NMR (400 MHz, CDCl$_3$) δ: 3.8 (s, COOCH$_3$, 3H), 4.9 (s, ArCH2O, 2H), 5.01 (s, ArCH2O, 4H), 7.1-7.3 (m, ArH & PhH, 17H); $^{13}$C NMR (100 MHz, CDCl$_3$) δ: 52.25, 71.27, 75.15, 109.13, 125.26, 127.57, 127.96, 128.04, 128.21, 128.56, 136.69, 137.48, 142.46, 152.59, 166.66; IR (KBr) ν=3064, 3031, 2947, 2878, 1715, 1589, 1499, 1453, 1110 and 754 cm$^{-1}$.

Preparation of G$_1$TNHNH$_2$ (b)

Compound (AB)$_3$G$_1$-COOCH$_3$ (4 g, 0.0088 mole) and hydrazine monohydrate (22 mL, 0.44 mole) were dissolved in MeOH (30 mL) and THF (15 mL). The reaction mixture was stirred at 70° C. for 12 hours. After the heating was stopped, the reaction mixture was allowed to cool to room temperature, and the volatiles were removed under reduced pressure. The residue was dissolved in CH$_2$Cl$_2$ and washed with H$_2$O. The organic layer was then dried over anhydrous Na$_2$SO$_4$, and the solvent was evaporated to get crude product, which was purified by column chromatography using silica gel as the stationary phase and 5% MeOH in CH$_2$Cl$_2$ as the eluent to get the pure product as a white powder (3.75 g, 93%); $^1$H-NMR (400 MHz, CDCl$_3$) δ: 5.03 (s, ArCH$_2$O, 6H), 6.96 (s, ArH, 2H), 7.18-7.30 (m, PhH, 15H); $^{13}$C NMR (100 MHz, CDCl$_3$) δ: 71.54, 75.31, 106.96, 127.60, 128.09, 128.19, 128.32, 128.69, 136.70, 137.52, 141.72, 142.57, 153.03, 168.44; IR(KBr) ν=3282, 3195, 3110, 3089, 3063, 3030, 3007, 2940, 2870, 1631, 1583, 1518, 1498, 1455, 1423, 1153 and 779 cm$^{-1}$; HRMS (ES+): m/z Calcd. for C$_{24}$H$_{26}$N$_2$O$_4$: 454.1893, found: 455.1964[M+H]$^+$; m.p. 122° C.

Preparation of Compound I

A solution of 9-anthracene carboxaldehyde (0.229 g, 0.0011 mole) in methanol was added drop wise to a $CHCl_3$ solution of compound b (0.50 g, 0.0011 mole). The mixture was stirred for 1 hour and the resulting gel was dried under vacuum to yield I (0.68 g, 96%). $^1$H-NMR (400 MHz, DMSO-$d_6$) δ: 4.98 (s, ArCH$_2$O, 2H), 5.19 (s, ArCH$_2$O, 4H), 7.28-7.65 (m, ArH, PhH & AnH, 21H), 8.07 (dd, J=6.0 Hz, J=2.0 Hz, AnH, 2H), 8.50 (s, AnH, H), 8.91 (d, J=7.6 Hz, AnH, 2H), 9.43 (s, CH=N, 1H); $^{13}$C NMR (100 MHz, DMSO-$d_6$) δ: 70.11, 74.28, 107.03, 125.34, 125.98, 126.30, 126.54, 127.69, 127.84, 128.12, 128.16, 128.44, 128.59, 129.40, 131.28, 137.46, 137.91, 143.49, 151.23, 168.65; HRMS (ES+): m/z Calcd. for $C_{43}H_{34}N_2O_4$: 642.2519 found: 643.2592[M+H]$^+$; m.p. 240° C.

Example 2

Synthetic Procedure for Compound II (Scheme 7)

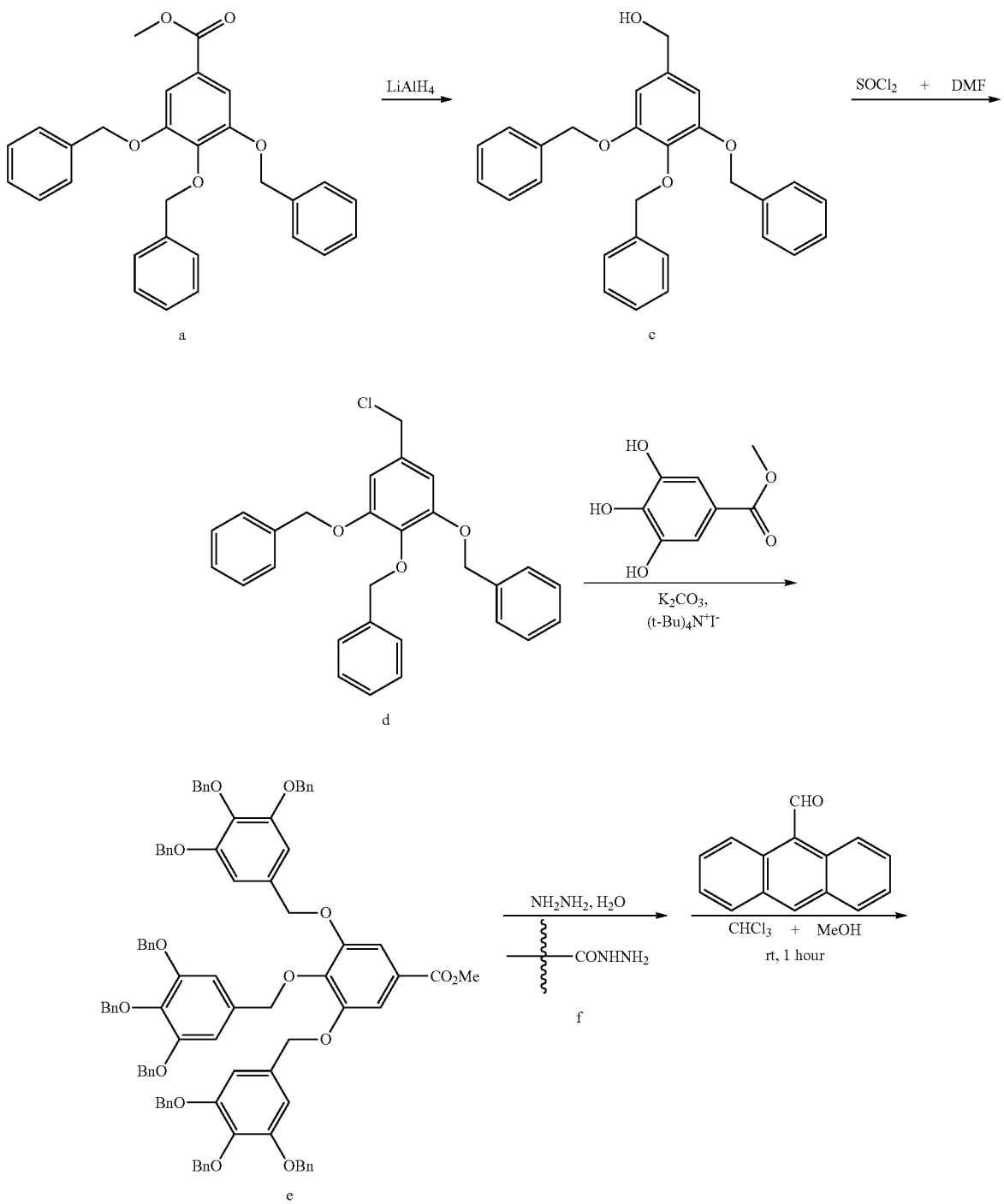

-continued

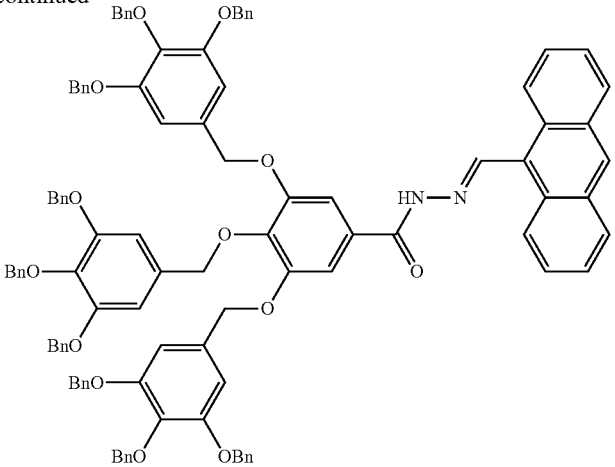

II

Preparation of (AB)$_3$G$_1$-CH$_2$OH (c)

Lithium aluminum hydride (0.809 g, 0.0213 mole) was suspended in 40 mL of freshly distilled THF in a dry three-neck round-bottom flask under nitrogen atm. (AB)$_3$ G$_1$-COOCH$_3$ (9 g, 0.0198 mole) was dissolved in 50 mL of freshly distilled THF and added drop wise to the lithium aluminum hydride solution. The reaction mixture was refluxed with stirring for 2 hours. The THF solution was cooled to room temperature and transferred to a beaker. Water was added drop wise to the vigorously stirred THF solution until the gray color of the lithium aluminum hydride was disappeared and a white solid was formed which is filtered and washed with THF. Excess solvent was removed under reduced pressure and the crude product was recrystallized from 95% methanol/water mixture to get the pure product ((AB)$_3$ G$_1$-CH$_2$OH) (7.6 g, 90%); $^1$H NMR (400 MHz, CDCl$_3$) δ: 4.6 (s, CH$_2$OH, 2H), 5.09 (s, ArCH$_2$O, 2H), 5.15 (s, ArCH$_2$O, 4H), 6.72 (s, ArH, 2H), 7.30-7.48 (m, PhH, 15H); $^{13}$C NMR (100 MHz, CDCl$_3$) δ: 65.42, 71.22, 75.26, 106.46, 127.45, 127.83, 127.90, 128.18, 128.52, 128.62, 136.66, 137.13, 137.81, 137.87, 153.02.

Preparation of [(AB)$_3$ G$_1$-Cl] (d)

To a solution of (AB)$_3$G$_1$-CH$_2$OH (5 g, 0.0117 mole) in dichloromethane (40 mL) was added a catalytic amount of DMF (3 mL) followed by SOCl$_2$ (1.6 mL, 0.014 mole) with stirring. The reaction mixture was stirred at room temperature for 2 hours. The solvent and excess SOCl$_2$ were distilled out under reduced pressure. The resulting yellow solid was dissolved in diethyl ether and washed with water and the organic layer was dried over Na$_2$SO$_4$. The solvent was removed under reduced pressure and directly used for further step.

Preparation of (AB)$_3$G$_2$-COOCH$_3$ dendron (e)

Methyl-3,4,5-trihydroxy benzoate (0.61 g, 0.0034 mole) and K$_2$CO$_3$ (3.31 g, 0.0204 mole) in 35 mL dry acetone were taken in a 100 mL round bottom flask. (AB)$_3$G$_1$-Cl (4.5 g, 0.010 mole) was added followed by the addition of a catalytic amount of tertiary butyl ammonium iodide (0.365 g, 0.001 mole). The solution was heated to reflux with stirring for 24 hours. After completion of reaction, the reaction mixture was cooled to room temperature and filtered. The filtered salts were further washed twice with dichloromethane. The solvent was then removed under reduced pressure using a rotary evaporator, yielding an oily substance that turned into a solid upon standing. The solid was recrystallized from hexane: toluene mixture (70:30). The yield of the product {(AB)$_3$ G$_2$-COOCH$_3$} was 4.2 g (89.3%); $^1$H NMR (400 MHz, CDCl$_3$) δ: 3.82 (s, COOCH$_3$, 3H), 4.75-4.93 (s, ArCH$_2$O, 24H), 6.66 (s, ArH, 2H) 6.68 (s, ArH, 4H), 7.10-7.29 (m, ArH & PhH, 47H); $^{13}$C NMR(100 MHz, CDCl$_3$) δ: 52.31, 71.03, 71.25, 71.49, 75.10, 75.21, 107.03, 107.65, 109.71, 125.44, 127.45, 127.49, 127.67, 127.77, 127.88, 128.10, 128.16, 128.40, 128.49, 132.29, 133.06, 136.99, 137.03, 137.92, 138.30, 142.43, 152.51, 152.83, 153.11, 166.51; IR(KBr) ν=3088, 3062, 3030, 2934, 2864, 1719, 1591, 1504, 1454, 1435, 1112 and 733 cm$^{-1}$.

Preparation of G$_2$TNHNH$_2$ (f)

Compound (AB)$_3$ G$_2$-COOCH$_3$ (3 g, 0.0021 mole) and hydrazine monohydrate (5.3 mL, 0.11 mole) were placed in a round bottomed flask and dissolved in MeOH (20 mL) and THF (20 mL). The reaction mixture was stirred at 70° C. for 12 hours. The heating was stopped, the reaction mixture was allowed to cool to room temperature, the volatiles were removed under reduced pressure, and the product was dissolved in CH$_2$Cl$_2$ and washed with H$_2$O. The organic layer was dried over anhydrous Na$_2$SO$_4$, and the solvent was evaporated to get crude product, which was purified by column chromatography using silica gel as the stationary phase and 5% MeOH in CH$_2$Cl$_2$ as the eluent to get the pure product as a white powder (2.71 g, 93.3%); $^1$H NMR (400 MHz, CDCl$_3$) δ: 4.73-4.89 (m, ArCH$_2$O, 24H), 6.63-6.65 (m, ArH, 6H), 6.94 (s, ArH, 2H), 7.13-7.32 (m, PhH, 45H); $^{13}$C NMR (100 MHz, CDCl$_3$) δ: 71.05, 71.25, 71.63, 75.19, 75.26, 106.91, 107.28, 107.61, 127.51, 127.73, 127.83, 127.94, 128.16, 128.21, 128.45, 128.55, 132.24, 133.08, 136.98, 137.03, 137.91, 138.31, 141.53, 152.90, 153.15, 168.13; IR(KBr) ν=3286, 3109, 3088, 3062, 3030, 2932, 2865, 1637, 1590, 1505, 1454, 1435, 1121 and 733 cm$^{-1}$; HRMS (ES+): m/z Calcd. for C$_{91}$H$_{80}$N$_2$O$_{13}$: 1408.5660, found: 1410.5817; m.p. 120° C.

Preparation of Compound II

A solution of 9-anthracene carboxaldehyde (0.148 g, 0.00071 mole) in methanol was added drop wise to a CHCl$_3$ solution of compound f (1 g, 0.00071 mole) under nitrogen atmosphere. The mixture was stirred for 1 hour and the resulting gel was dried under vacuum to yield II (1.07 g, 94%); $^1$H NMR (400 MHz, CDCl$_3$) δ: 4.63-4.91 (s, ArCH$_2$O, 24H), 6.53-6.67 (m, ArH, 6H), 7.08-7.48 (m, ArH, PhH & AnH, 51H), 7.86 (d, AnH, J=8.0 Hz, 2H), 8.35 (s, AnH, 1H), 8.41 (s, AnH, 2H), 9.40 (s, CONH, 1H), 9.68 (s, CH=N, 1H); $^{13}$C NMR (100 MHz, CDCl$_3$) δ: 70.95, 71.08, 71.43, 75.10, 75.21, 106.87, 107.07, 107.31, 107.74, 124.87, 125.29, 127.06, 127.55, 127.75, 127.87, 128.14, 128.38, 128.46, 128.90, 130.13, 130.28, 132.33, 136.88, 137.86, 138.03, 138.17, 148.36, 152.89, 153.04, 164.29; MS (MALDI-TOF): m/z Calcd. for $C_{106}H_{88}N_2O_{13}$: 1597, found: 1698.4[M+H]+, 1620.3[M+Na]+; m.p. 137° C.

Example 3

Synthetic Procedure for Compound III (Scheme 8)

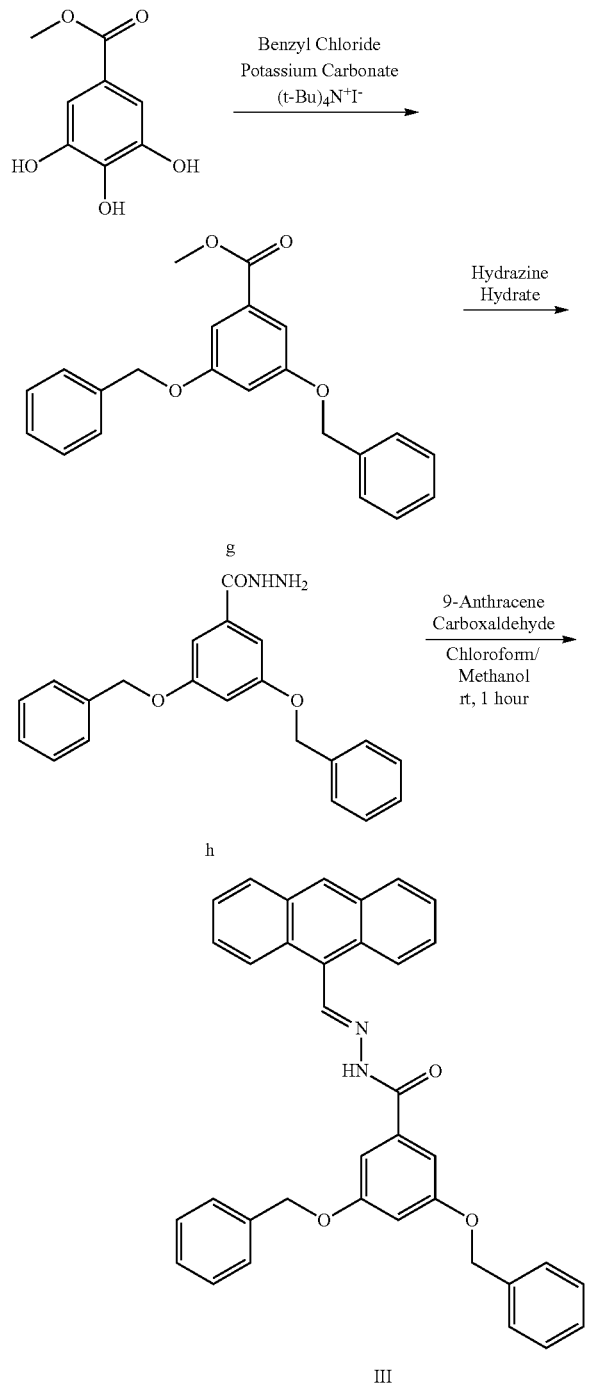

Preparation of $(AB)_2G_1$-$COOCH_3$ (g)

Methyl-3,5-dihydroxybenzoate (8 g, 0.0476 mole) and potassium carbonate (13.2 g, 0.0952 mole) were taken in 130 mL of 1,4-dioxane in a 250 mL round bottom flask. Benzyl chloride (10.95 mL, 0.0952 mole) was added followed by the addition of a catalytic amount of tertiary butyl ammonium iodide (1.5 g, 0.0047 mole). The solution was heated to reflux with stirring for 24 hours. The solvent was then removed under reduced pressure using a rotary evaporator to get an oily substance that turned into a solid upon standing. The solid was crystallized from methanol to get $(AB)_2G_1$-$COOCH_3$ (15 g, 90.9%); $^1$H NMR (400 MHz, CDCl$_3$) δ: 3.80 (s, COOCH$_3$, 3H), 4.97 (s, ArCH$_2$O, 4H), 6.71 (s, ArH, 1H), 7.23-7.34 (m, ArH &PhH, 12H); $^{13}$C NMR (100 MHz, CDCl$_3$) δ: 52.29, 70.34, 107.32, 108.46, 127.60, 128.15, 128.50, 128.67, 132.12, 136.54, 159.86, 166.80; IR(KBr) ν=3095, 3062, 3027, 2949, 2905, 2862, 1714, 1596, 1499, 1472, 1439, 1106 and 761 cm$^{-1}$.

Preparation of $G_1$ $DNHNH_2$ (h)

Compound $(AB)_2$ $G_1$-$COOCH_3$ (4 g, 0.011 mole) and hydrazine monohydrate (27.5 mL, 0.55 mole) were dissolved in MeOH (30 mL) and THF (15 mL). The reaction mixture was stirred at 70° C. for 12 hours. After the heating was stopped, the reaction mixture was allowed to cool to room temperature, and the volatiles were removed under reduced pressure. The residue was dissolved in CH$_2$Cl$_2$ and washed with H$_2$O. The organic layer was then dried over anhydrous Na$_2$SO$_4$, and the solvent was evaporated to get crude product, which was purified by column chromatography using silica gel as the stationary phase and 5% MeOH in CH$_2$Cl$_2$ as the eluent to get the pure product as a white powder (3.8 g, 95%); $^1$H NMR (400 MHz, CDCl$_3$) δ: 4.87 (s, ArCH$_2$O, 4H), 6.63 (s, ArH, 1H), 6.90 (s, ArH, 2H), 7.09-7.27 (m, PhH, 10H); $^{13}$C NMR (100 MHz, CDCl$_3$) δ: 70.40, 105.77, 106.14, 127.32, 127.63, 128.25, 128.73, 134.86, 136.49, 160.19, 168.49; IR(KBr) ν=3287, 3088, 3062, 3030, 2923, 2858, 1637, 1591, 1514, 1497, 1453, 1436, 1112 and 795 cm$^{-1}$; HRMS (ES+): m/z Calcd. for $C_{21}H_{20}N_2O_3$: 348.1474, found: 349.1562[M+H]+.

Preparation of Compound III

A solution of 9-anthracene carboxaldehyde (0.59 g, 0.0028 mole) in methanol was added drop wise to a CHCl$_3$ solution of compound h (1 g, 0.0028 mole). The mixture was stirred for 1 hour and the resulting gel was dried under vacuum to yield III (1.45 g, 96%); $^1$H NMR (400 MHz, DMSO-d$_6$) δ: 5.12 (s, ArCH$_2$O, 4H), 6.56 (s, ArH, 1H), 7.32-7.52 (m, ArH, PhH & AnH, 16H), 8.06 (dd, J=8.0 Hz, J=3.6 Hz, AnH, 2H), 8.49 (s, AnH, H), 8.93 (d, J=6.0 Hz, AnH, 2H), 9.39 (s, CH=N, 1H); $^{13}$C NMR (100 MHz, DMSO-d$_6$) δ: 69.24, 102.29, 107.04, 125.32, 125.97, 126.30, 126.55, 127.69, 127.80, 128.47, 128.57, 129.39, 129.49, 131.27, 137.38, 143.60, 144.15, 158.63, 168.55; HRMS (ES+): m/z Calcd. for $C_{36}H_{28}N_2O_3$: 536.2100, found: 537.2178[M+H]+; m.p. 263° C.

Example 4
Synthetic Procedure for Compound IV (Scheme 9)
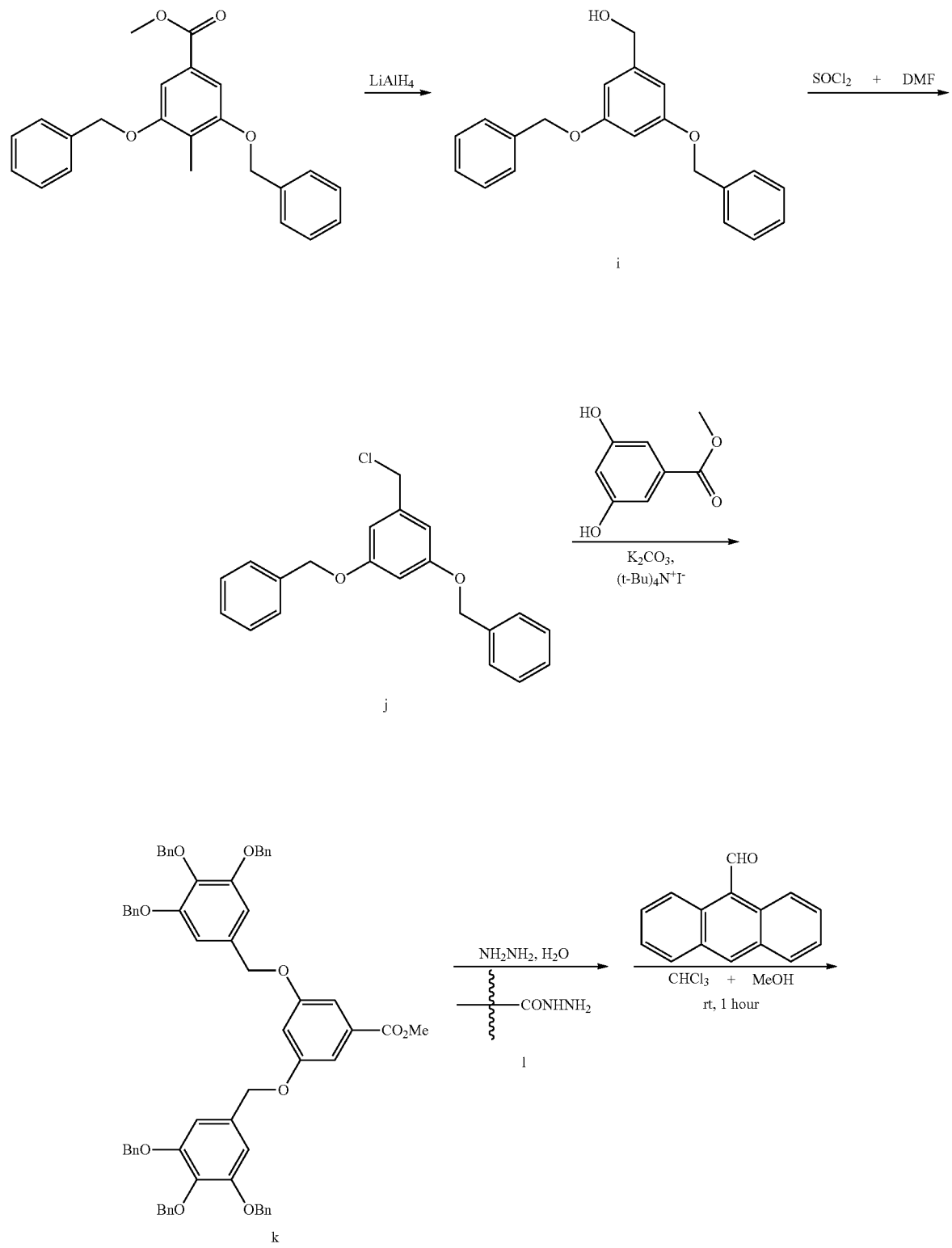

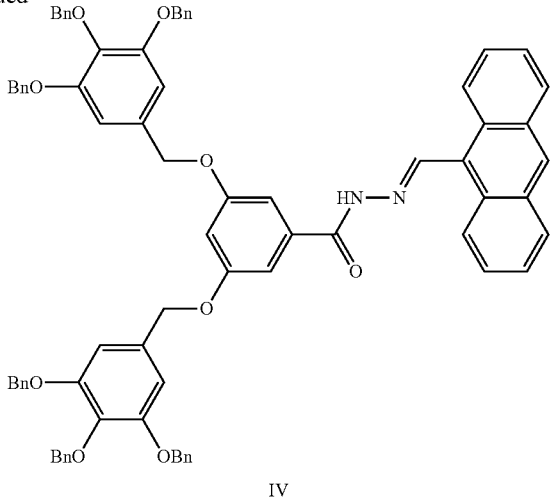

IV

Preparation of (AB)₂ G₁-CH₂—OH (i)

Lithium aluminum hydride (1.54 g, 0.0405 mole) was suspended into 50 mL of freshly distilled THF in a dry three-neck round-bottom flask under nitrogen atm. (AB)₂G₁-COOCH₃ (13.1 g, 0.0376 mole) was dissolved in 60 mL of freshly distilled THF and added drop wise to the lithium aluminum hydride solution. The reaction mixture was heated to reflux with stirring for 2 hours. The THF solution was cooled to room temperature and transferred to a beaker. Water was added drop wise to the vigorously stirred THF solution until the gray color of the lithium aluminum hydride was disappeared and a white solid was formed which is filtered and washed with THF, Excess solvent was removed under reduced pressure and the crude product was recrystallized from 95% methanol/water mixture to get the alcohol (AB)₂G₁-CH₂—OH with yield 10.9 g (90.6%); ¹H NMR (400 MHz, CDCl₃) δ: 4.54 (s, CH₂OH, 2H), 4.95 (s, ArCH₂O, 4H), 6.47-6.54 (s, ArH, 3H), 7.17-7.34 (m, PhH, 10H); ¹³C NMR (100 MHz, CDCl₃) δ: 65.34, 70.13, 101.39, 105.82, 127.54, 128.03, 128.62, 136.89, 143.47, 160.22.

Preparation of (AB)₂G₁-CH₂Cl (j)

To a solution of (AB)₂ G₁-CH₂—OH (7 g, 0.0218 mole) in dichloromethane (40 mL), a catalytic amount of DMF and SOCl₂ (1.95 mL, 0.026 mole) were added with stirring. It was stirred at room temperature for 2 hours. The solvent and excess SOCl₂ were distilled out under reduced pressure. The resulting yellow solid was dissolved in diethyl ether, washed with water and the organic layer was dried over Na₂SO₄. The solvent was removed under reduced pressure and directly used to further step.

Preparation of (AB)₂G₂-COOCH₃ dendron (k)

Methyl-3,5-dihydroxy benzoate (1.9 g, 0.0118 mole) and K₂CO₃ (3.9 g, 0.0283 mole) in 35 mL dry acetone were taken in a 250 mL round bottom flask. (AB)₂G₁-CH₂Cl (8 g, 0.0236 mole) was added followed by the addition of a catalytic amount of tertiary butyl ammonium iodide (0.358 g, 0.001 mole). The solution was heated to reflux for 24 hours. After completion of reaction, the reaction mixture was cooled to room temperature and filtered. The filtered salts were further washed twice with dichloromethane. The solvent was then removed under reduced pressure to afford an oil that turned into a solid upon standing. The solid was recrystallized from hexane:toluene mixture (70:30) with a yield of 7.9 g (89.4%); ¹H NMR (400 MHz, CDCl₃) δ: 3.96 (s, COOCH3, 3H), 5.06-5.09 (s, ArCH2O, 12H), 6.63-6.82 (s, ArH, 7H), 7.30-7.47 (m, ArH & PhH, 22H); ¹³C NMR (100 MHz, CDCl3) δ: 52.39, 70.27, 101.85, 106.54, 07.33, 108.54, 127.67, 128.14, 128.72, 132.21, 136.90, 139.02, 159.83, 160.33, 166.85; IR (KBr) ν=3089, 3061, 3029, 3006, 2948, 2910, 2871, 1712, 1520, 1497, 1438, 1110 and 769 cm⁻¹.

Preparation of G₂DNHNH₂ (l)

Compound (AB)₂G₂-COOCH₃ (3.5 g, 0.0045 mole) and hydrazine monohydrate (11.3 mL, 0.22 mole) were placed in a round bottomed flask and dissolved in MeOH (20 mL) and THF (20 mL). The reaction mixture was stirred at 70° C. for 12 hours. The heating was stopped, the reaction mixture was allowed to cool to room temperature, the volatiles were removed under reduced pressure, and the product was dissolved in CH₂Cl₂ and washed with H₂O. The organic layer was dried over anhydrous Na₂SO₄, and the solvent was evaporated to get crude product, which was purified by column chromatography using silica gel as the stationary phase and 5% MeOH in CH₂Cl₂ as the eluent to get the pure product as a white powder (3.2 g, 91.4%); ¹H NMR (400 MHz, CDCl₃) δ: 4.83-4.93 (s, ArCH2O,12H), 6.48-6.85 (s, ArH, 9H), 7.16-7.32 (m, PhH, 20H); ¹³C NMR ((100 MHz, CDCl₃) δ: 70.16, 101.67, 105.62, 106.00, 106.39, 127.19, 127.61, 128.08, 128.25, 128.48, 128.64, 134.78, 136.73, 138.79, 160.02, 160.23, 168.44; IR(KBr) ν=3332, 3088, 3060, 3030, 2909, 2866, 1654, 1596, 1519, 1497, 1446, 1156 and 732 cm⁻¹; HRMS (ES+): m/z Calcd. for C₄₉H₄₄N₂O₇: 772.3149, found: 773.3215[M+H]⁺; m.p. 110° C. m.p. 127° C.

Preparation of Compound IV

A solution of 9-anthracene carboxaldehyde (0.269 g, 0.0013 mole) in methanol was added drop wise to a CHCl₃ solution of compound 1 (1 g, 0.0013 mole). The mixture was stirred for 1 hour and the resulting gel was dried under vacuum to yield IV (1.17 g, 93%); ¹H NMR (400 MHz, CDCl₃) δ: 4.95 (s, ArCH₂O, 12H), 6.50-6.68 (m, ArH, 7H), 7.08-7.46 (m, ArH, PhH & AnH, 26H), 7.92 (s, AnH, 2H), 8.42 (s, AnH, 1H), 8.55 (s, AnH, 2H), 9.43 (s, CH=N, 1H); ¹³C NMR (100 MHz, CDCl₃) δ: 70.28, 101.80, 106.56, 125.51, 126.20, 127.30, 127.70, 127.77, 127.96, 128.17, 128.37, 128.58, 128.73, 128.74, 129.09, 130.49, 131.39, 136.86, 139.00, 160.29, 160.35, 168. MS (MALDI-TOF): m/z Calcd. for C₆₄H₅₂N₂O₇: 960, found: 961.3[M+H]⁺, 983.2[M+Na]⁺, 999.5[M+K]⁺; m.p. 156° C.

Example 5

Determining Critical Gel Concentrations

Critical gel concentration:

Gelation and the critical gel concentration was determined for representative compounds I-IV. At the critical gel concentration, the gelator was found to be initially insoluble in the solvent or solvent mixture at room temperature, but upon gentle heating, a clear solution was formed. On cooling to room temperature, a gel was formed. Critical gel concentrations for compounds I-IV in selected solvents and solvent mixtures are presented in Table 1.

TABLE 1

Gelation properties and critical gel concentrations (CGCs) of dendrimers in various organic solvents and mixed solvents at 25° C.

| Solvent | I | II | III | IV |
| --- | --- | --- | --- | --- |
| Chloroform | G (8 mg/mL) | S | G (7 mg/mL) | G (4 mg/mL) |
| Dichloromethane | G (10 mg/mL) | S | P.G | T.G (5 mg/mL) |
| Tetrahydrofuran | G (4 mg/mL) | S | P.G | S |
| Dioxane | G (5 mg/mL) | S | P.G | S |
| Acetone | G (6 mg/mL) | G (4 mg/mL) | P.G | G (5 mg/mL) |
| Dimethylformamide | S | S | P | S |
| Ethyl Acetate | G (6 mg/ml) | T.G (3 mg/mL) | G (6 mg/mL) | T.G (5 mg/ml) |
| Methanol | G (5 mg/mL) | P.G | P.G | P |
| Ethanol | G (4 mg/mL) | P.G | P.G | G (15 mg/mL) |
| Benzene | P.G | T.G (4 mg/mL) | P | T.G (4.5 mg/mL) |
| Toluene | P.G | T.G (3 mg/mL) | P | T.G (5 mg/mL) |
| Chlorobenzene | G (15 mg/mL) | P.G | P | T.G (6 mg/mL) |
| Benzyl alcohol | G (5 mg/mL) | G (4 mg/mL) | P | T.G (7 mg/mL) |
| Xylene | P | T.G (6 mg/mL) | P | P.G |
| Anisole | G (6 mg/mL) | G (10 mg/mL) | P | G (15 mg/mL) |
| Pyridine | G (3.5 mg/mL) | S | P.G | S |
| Dimethylformamide:Water | G (3 mg/mL) (1:1) | G (4 mg/mL) | G (6 mg/mL) (1:1) | G (7 mg/mL) (1:1) |
| Tetrahydrofuran:Water | G (2 mg/mL) (1:1) | G (2.5 mg/mL) | P.G | G (8 mg/mL) (1:1) |
| Dioxane:Water | G (2.5 mg/mL) (1:1) | P | G (8 mg/mL) | G (5 mg/mL) (1:1) |
| Chloroform:Water | G (4 mg/mL) (1:1) | G (3 mg/mL) (1:1) | P.G | G (2.5 mg/mL) (1:1) |

G = Gelation,
T.G = Transparent gelation,
S = Solution,
P = Precipitation,
P.G = Partial gelation

Example 6

Concentration Effect on Critical Gel Temperature

A mixture of compound I was prepared as in Example 1 in a chloroform-methanol mixture (1:1% v/v) for 1 hour at room temperature to yield a robust gel in the reaction flask. The gel from the mixture was dried under vacuum and then dissolved in a 1:1 tetrahydrofuran:water mixture at 2 mg/mL concentration increments from 2 mg/mL to 12 mg/mL. The gelation temperature was determined by heating to form a solution and cooling as described in Example 5. The observed gelation temperature increased from 60° C. to 70° C. over the concentration range.

Example 7

Fluoride Ion Detection

A mixture of compound I was prepared as in Example 1 in a chloroform-methanol mixture (1:1% v/v) for 1 hour at room temperature to yield a robust gel in the reaction flask. The gel from the mixture was dried under vacuum and then dissolved in a tetrahydrofuran at 4 mg/mL with heating. On cooling to room temperature, a yellow gel was formed. Upon addition of one equivalent of tetrabutylammonium fluoride (TBAF), the interface surface of the gel began to turn red after one minute. After three minutes, one half of the gel was red colored. After ten minutes, the mixture was red colored throughout and the gel changed to a liquid. Upon addition of 0.2 mL of water, the mixture became a yellow gel.

Example 8

Selective Fluoride Ion Detection

A mixture of compound I was prepared as in Example 1 in a chloroform-methanol mixture (1:1 v/v) for 1 hour at room temperature to yield a robust gel in the reaction flask. The gel from the mixture was dried under vacuum and then dissolved in a tetrahydrofuran at 4 mg/mL with heating. On cooling to room temperature, a yellow gel was formed. Upon addition of 0.1 equivalents of selected anions (chloride, bromide, iodide, perchlorate, acetate, dihydrogen phosphate, bisulfate) as tetrabutylammonium salts to individual samples of the gel, there was no visible change observed in the samples. UV-Vis spectra were obtained on the resultant gel mixtures (FIG. 1). Upon addition of 0.1 equivalents of tetrabutylammonium fluoride, the gel became red colored and the preformed gel was disrupted.

Example 9

Assay for Fluoride Ion

Gels of compound III (28 mg) are prepared in ethyl acetate (4 mL) as per Example 8. About 250 μL of test sample (tetrahydrofuran containing unknown concentration of fluoride ions) is added to the gel. Similarly, standards are prepared using 250 μL aliquots of THF of various concentrations of TBAF (corresponding to about 1, 0.3, 0.1 and 0.01 equivalents fluoride per equivalent of compound III, respectively), are added to similar gels of compound III.

The color change, intensity, and consistency of the resulting vial contents is compared with the reference samples to give the concentration of the sample of unknown concentration. The comparison may be visual, as a comparison to the closest color to give an approximate concentration of fluoride ion in the sample. Visual comparison allows for measurement in the field where there may be no reliable power. Alternatively, plotting the absorbance measurement of the references, as determined on a spectrophotometer, a calibration curve may be established. The fluoride ion content of the sample may be obtained by comparison of the sample's absorbance to the calibration curve.

Example 10

Fluoride Ion Detection Kit

A kit containing compound II, vials, THF, and instructions is used to prepare solutions of compound II (5.5 mg) in THF (10 mL) to give $1\times10^{-4}$ M mixtures in four vials. To three vials are added one equivalent, 0.5 equivalent, and 0.1 equivalent of fluoride ion in THF. The contents of the three vials become bright red, red, and light red, respectively, as the concentration of fluoride ion decreases. A sample of unknown concentration of fluoride ions is added to the fourth vial. The sample concentration may be determined by visual comparison or by the calibration curve method as per Example 9.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). While various compositions, methods, and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups. It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

What is claimed is:

1. A method of detecting fluoride ions in a sample, the method comprising:
providing a sample suspected of containing fluoride ions;
contacting the sample with compound according to the formula (XX):

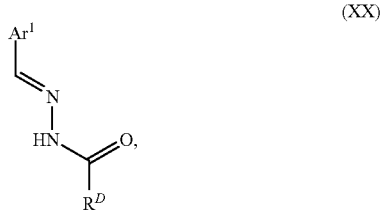

(XX)

a tautomer thereof, or a salt thereof, wherein $Ar^1$ is a —$C_{10}$-$C_{36}$ polycyclic aromatic hydrocarbon, optionally substituted with one or two $R^0$ groups;

each $R^0$ is independently trifluoromethyl, trifluoroethyl, nitro, cyano, —OH, or —$C_1$-$C_{20}$alkyl;

$R^D$ is a dendrimer comprising a phenyl core, a first generation layer of —O—($C_1$-$C_{12}$)alkyl-aryl bonded to the core, and an optional second generation layer of —O—($C_1$-$C_{12}$)alkyl-aryl bonded to the first generation layer aryl; and detecting at least one of a visual color change and a phase change, wherein such change indicates fluoride ions are present in the sample.

2. The method of claim 1, wherein the visual color change is a red-shift.

3. The method of claim 1, wherein the phase change is from a gel to a liquid.

4. The method of claim 1, wherein the fluoride ions are present in the sample at a concentration of at least about 1 micromolar.

5. The method of claim 1, wherein the fluoride ions are present at a concentration of at least 0.1 equivalents per equivalent of compound.

6. The method of claim 1, wherein the detecting is at least 100 fold more selective for the fluoride ions than to anions selected from the group consisting of chloride, bromide, iodide, perchlorate, acetate, dihydrogen phosphate, hydrogen phosphate, phosphate, bisulfate, sulfate, and combinations thereof.

7. The method of claim 1, further comprising the step of contacting the sample with water.

8. The method of claim 1, wherein the compound is solvated with at least one solvent selected from the group consisting of dimethyl sulfoxide, N,N-dimethylformamide, tetrahydrofuran, and acetonitrile.

* * * * *

UNITED STATES PATENT AND TRADEMARK OFFICE
CERTIFICATE OF CORRECTION

| | |
|---|---|
| PATENT NO. | : 8,828,735 B2 |
| APPLICATION NO. | : 13/528981 |
| DATED | : September 9, 2014 |
| INVENTOR(S) | : Edamana et al. |

Page 1 of 4

It is certified that error appears in the above-identified patent and that said Letters Patent is hereby corrected as shown below:

Please delete the Title page and insert the Title Page showing the illustrative figure shown on the attached Title page.

On the Title Page, in item (56), under "PUBLICATIONS", in Column 2, Line 1, delete "Rajamilli P. et al," and insert -- Rajamalli P. et al., --, therefor.

On the Title Page, in item (57), under "ABSTRACT", in Column 2, Line 3, delete "sample" and insert -- sample. --, therefor.

In the Drawings:

Delete fig. 1 and substitute therefor the drawing sheet, consisting of fig. 1 as shown on the attached page.

In the Specification:

In Column 3, Line 61, delete "dendrimirs" and insert -- dendrimers --, therefor.

In Column 4, Line 4, delete "a acyl-hydrazone" and insert -- an acyl-hydrazone --, therefor.

In Column 7, Line 34, delete "I⁻," and insert -- I⁻,ClO₄⁻ --, therefor.

In Column 7, Line 39, delete "F not" and insert -- F⁻ not --, therefor.

In Column 12, Line 42, delete "N-(" and insert -- N'-( --, therefor.

In Column 12, Line 43, delete "N-(" and insert -- N'-( --, therefor.

Signed and Sealed this
Twelfth Day of May, 2015

Michelle K. Lee
*Director of the United States Patent and Trademark Office*

CERTIFICATE OF CORRECTION (continued)

U.S. Pat. No. 8,828,735 B2

In Column 12, Line 44, delete "N-(" and insert -- N'-( --, therefor.

In Column 12, Line 46, delete "N-(" and insert -- N'-( --, therefor.

In Column 20, Line 33, delete "stiffing" and insert -- stirring --, therefor.

In Column 20, Line 39, delete "ArCH2O," and insert -- ArCH$_2$O, --, therefor.

In Column 20, Line 40, delete "ArCH2O," and insert -- ArCH$_2$O, --, therefor.

In Column 20, Line 59, delete "1H-NMR" and insert -- 1H NMR --, therefor.

In Column 21, Line 6, delete "1H-NMR" and insert -- 1H NMR --, therefor.

In Column 23, Line 49, delete "stiffing." and insert -- stirring. --, therefor.

In Column 23, Line 60, delete "stiffing" and insert -- stirring --, therefor.

In Column 29, Line 30, delete "stiffing" and insert -- stirring --, therefor.

In Column 29, Line 47, delete "stiffing." and insert -- stirring. --, therefor.

In Column 29, Line 67, delete "COOCH3," and insert -- COOCH$_3$, --, therefor.

In Column 30, Line 23, delete "ArCH2O," and insert -- ArCH$_2$O, --, therefor.

In Column 30, Line 24, delete "CDCl3)" and insert -- CDCl$_3$) --, therefor.

In Column 30, Line 44, delete "ArCH2O," and insert -- ArCH$_2$O, --, therefor.

(12) United States Patent
Edamana et al.

(10) Patent No.: US 8,828,735 B2
(45) Date of Patent: Sep. 9, 2014

(54) VISUAL DETECTION OF FLUORIDE IONS

(75) Inventors: Prasad Edamana, Chennai (IN); Rajamalli Pachaiyappan, Kottappoondi (IN)

(73) Assignee: Indian Institute of Technology Madras, Tamilnadu, Chennai (IN)

(*) Notice: Subject to any disclaimer, the term of this patent is extended or adjusted under 35 U.S.C. 154(b) by 0 days.

(21) Appl. No.: 13/528,981

(22) Filed: Jun. 21, 2012

(65) Prior Publication Data

US 2013/0344608 A1   Dec. 26, 2013

(51) Int. Cl.
*G01N 21/29* (2006.01)

(52) U.S. Cl.
USPC ............................................................ 436/124

(58) Field of Classification Search
CPC ........ G01N 21/29; G01N 21/25; G01N 21/17; G01N 21/00
USPC ............................................................ 436/124

See application file for complete search history.

(56) References Cited

PUBLICATIONS

Rajamilli P. et al, Low Molecular Weight Fluorescent Organogel for Fluoride Ion Detection, Organic Letters, received May 21, 2011, published Jun. 21, 2011, vol. 13, No. 14, p. 3714-3717.*

* cited by examiner

*Primary Examiner* — Christine T Mui
(74) *Attorney, Agent, or Firm* — Pepper Hamilton LLP

(57) ABSTRACT

Dendrimer-hydrazides are coupled to polycyclic aromatic hydrocarbons for use in the visual detection of the presence of low levels of fluoride in a sample. The dendrimers can have a phenyl core, a first generation of aralkyl ethers, and an optional second generation of aralkyl ethers. The compounds form gels with solvents. In the presence of fluoride ion, the gels undergo color changes and/or gel to liquid phase change.

8 Claims, 2 Drawing Sheets

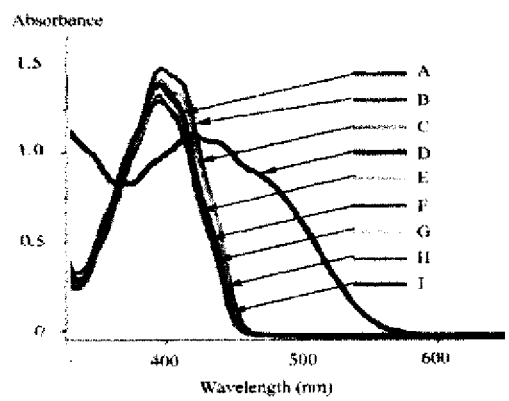

A = Compound I
B = Compound I + $CH_3COO^-$
C = Compound I + $Br^-$
D = Compound I + $F^-$
E = Compound I + $ClO_4^-$
F = Compound I + $I^-$
G = Compound I + $HSO_4^-$
H = Compound I + $Cl^-$
I = Compound I + $H_2PO_4^-$ A = Compound I
B = Compound I + $CH_3COO^-$
C = Compound I + $Br^-$
D = Compound I + $F^-$
E = Compound I + $ClO_4^-$
F = Compound I + $I^-$
G = Compound I + $HSO_4^-$
H = Compound I + $Cl^-$
I = Compound I + $H_2PO_4^-$